(12) United States Patent
Anderson et al.

(10) Patent No.: US 7,024,939 B2
(45) Date of Patent: Apr. 11, 2006

(54) METHOD AND APPARATUS FOR THE VARIABLE SPEED RING ROLLING SIMULATION OF SUBSTRATES

(75) Inventors: Barry Jay Anderson, Cincinnati, OH (US); Michael Joseph Lamping, Cincinnati, OH (US); Eugene Paul Daut, Cincinnati, OH (US); Randall Allen Myers, Indian Springs, OH (US); George Stephen Reising, Batavia, OH (US); Anand Rudra Venkitaraman, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 33 days.

(21) Appl. No.: 10/942,487

(22) Filed: Sep. 16, 2004

(65) Prior Publication Data
US 2005/0262948 A1    Dec. 1, 2005

Related U.S. Application Data

(63) Continuation-in-part of application No. 10/615,977, filed on Jul. 9, 2003, now Pat. No. 6,915,700, which is a continuation-in-part of application No. 10/422,879, filed on Apr. 24, 2003, which is a continuation-in-part of application No. 10/377,070, filed on Feb. 28, 2003, now Pat. No. 6,843,134.

(60) Provisional application No. 60/429,802, filed on Nov. 27, 2002.

(51) Int. Cl.
*G01L 1/00* (2006.01)
(52) U.S. Cl. .......................... 73/763; 100/48
(58) Field of Classification Search .................. 73/763, 73/769, 818, 824, 866; 100/48
See application file for complete search history.

(56) References Cited

U.S. PATENT DOCUMENTS

| | | | |
|---|---|---|---|
| 3,640,127 A | 2/1972 | Meissner | |
| 3,795,134 A | 3/1974 | Eichenbrenner et al. | |
| 4,116,892 A | 9/1978 | Schwarz | |
| 4,812,722 A | 3/1989 | Corrothers | |

(Continued)

FOREIGN PATENT DOCUMENTS

EP    1 043 579 A1    10/2000

(Continued)

OTHER PUBLICATIONS

U.S. Appl. No. 10/377,070, filed Feb. 28, 2003, Anderson et al.

(Continued)

*Primary Examiner*—Charles Garber
(74) *Attorney, Agent, or Firm*—George H. Leal; Jay A. Krebs; Ken K. Patel

(57) ABSTRACT

A method for inducing strain on a workpiece includes the step of providing a testing apparatus having a first set of teeth and a second set of teeth. The workpiece is placed adjacent to the first or second set of teeth. The second set of teeth is disposed on a movable carriage which linearly reciprocates thereby allowing the first and the second sets of teeth to engage and disengage each other. A commanded position by time is provided to the carriage while the actual position by time of the carriage is measured. The first set of teeth are in communication with at least one load cell such that when the first set of teeth engage the second set of teeth, the load applied by the carriage is measured. The actual position by time data and the load data are manipulated to produce vast information pertaining to the workpiece.

18 Claims, 24 Drawing Sheets

U.S. PATENT DOCUMENTS

| | | |
|---|---|---|
| 4,834,741 A | 5/1989 | Sabee |
| 5,143,679 A | 9/1992 | Weber et al. |
| 5,156,793 A | 10/1992 | Buell et al. |
| 5,167,897 A | 12/1992 | Weber et al. |
| 5,188,456 A | 2/1993 | Burke et al. |
| 5,351,553 A | 10/1994 | Lepie et al. |
| 5,422,172 A | 6/1995 | Wu |
| 5,515,294 A | 5/1996 | Mohr et al. |
| 5,518,801 A | 5/1996 | Chappell et al. |
| 5,575,078 A | 11/1996 | Moulton, III |
| 5,767,402 A | 6/1998 | Sandlass et al. |
| 6,370,962 B1 | 4/2002 | Sullivan et al. |
| 6,410,820 B1 | 6/2002 | McFall et al. |
| 6,500,377 B1 | 12/2002 | Schneider et al. |
| 6,537,401 B1 * | 3/2003 | Couillard et al. .............. 156/64 |

FOREIGN PATENT DOCUMENTS

| | | |
|---|---|---|
| WO | WO 99/56685 A1 | 11/1999 |

OTHER PUBLICATIONS

U.S. Appl. No. 10/422,879, filed Apr. 24, 2003, Anderson et al.

U.S. Appl. No. 10/615,977, filed Jul. 9, 2003, Anderson et al.

* cited by examiner

METHOD AND APPARATUS FOR THE VARIABLE SPEED RING ROLLING SIMULATION OF SUBSTRATES

CROSS REFERENCE TO RELATED APPLICATION

This application is a continuation-in-part of prior U.S. application Ser. No. 10/615,977, filed on Jul. 9, 2003 now U.S. Pat. 6,915,700; which is a continuation-in part of prior U.S. application Ser. No. 10/422,879 filed on Apr. 24, 2003; which is a continuation in part of U.S. application Ser. No. 10/377,070, filed on Feb. 28, 2003 now U.S. Pat. No. ,843,134, which claims benefit to Provisional Application U.S. Ser. No. 60/429,802, filed Nov. 27, 2002.

FIELD OF THE INVENTION

The present invention relates to a method and apparatus for the simulation of a ring rolling process on a workpiece. Specifically, the present invention pertains to a method and apparatus for simulating a ring rolling process on a workpiece at various speeds and more particularly to the method and apparatus for applying a variable strain and strain rate on workpieces.

BACKGROUND OF THE INVENTION

Absorbent articles are widely used by both infants and adults in order to receive and contain body exudates. Their wide spread use has spurred significant advances in the materials used to create the absorbent articles as well as the high speed processes by which these materials are created and assembled.

An example of such a material advancement is a stretchable deformable elastic laminate. Typically, elastic laminates comprise a non-elastic substrate bonded to an elastic member. The elastic laminates can be used in a wide variety of locations in an absorbent article. For example, the elastic laminates may be found in a side waist, a back waist, front waist, or crotch region.

One method of producing an elastic laminate involves providing "zero strain" stretch laminate webs which comprise at least two plies of material secured to one another along at least a portion of their coextensive surfaces while in a substantially untensioned ("zero strain") condition. At least one of the plies employed in the "zero strain" stretch laminate is comprised of a material which is stretchable and elastomeric, i.e., it will return substantially to its untensioned dimensions after an applied tensile force has been released. The second ply secured to the elastomeric ply is elongatable but not necessarily elastomeric. If the second ply is elongatable but not elastomeric, upon stretching, the second ply will permanently elongate at least to a certain degree, so that upon release of the applied tensile forces, it will not fully return to its original undistorted configuration.

The stretching can be induced by mechanical activation which may include meshing the laminate between corrugated mating rolls. This method is called ring rolling and is often performed at high speeds. As an example, a non-elastic material can be plastically deformed in a ring rolling process, thereby reducing the material thickness and creating thin spots in areas where meshing occurs. The laminate experiencing the ring rolling process can be exposed to very high strain rates.

In general, new materials, in order to be proven acceptable in the ring rolling process, are generally tested in the actual process. However, actual process or line testing can be associated with many problems. Specifically, a minimum length of material is needed to engage the ring rolling process. Subsequently, personnel can evaluate the new material downstream of the ring rolling process by counting pinholes or looking for other defects caused by the ring rolling process. Unfortunately, the incorporation of the new material into the process for testing purposes may cause interruptions to manufacturing lines and may require significant personnel time and cost. Moreover, while laminate structures can be tested in the actual process, it is difficult to isolate the effects of various components of the laminate structure. For example, a laminate structure comprising a first nonwoven layer and a second nonwoven layer adhesively bonded together can be tested in the ring rolling process. However, it may be difficult or impossible to isolate the effect of the adhesive on a nonwoven by running the laminate structure through the ring rolling process.

Alternatively, there are some conventional methods of testing new materials. Specifically, new materials can be tested on a tensile tester. While the tensile tester can provide useful information about the new material, the tensile tester may not be able to achieve the strain rates that the new material would be subjected to during an actual ring rolling process. In general, a material can experience strain rates in excess of $1000 \ s^{-1}$ when subjected to an actual ring rolling process.

Moreover, tensile testers may also be limited by a minimum gage length of a sample. The gage length of a material in a standard ring rolling process may be much smaller than 2.0 mm. On a tensile tester, a test sample with a gage length of less than 2 mm may prove difficult to mount on the tensile tester. In addition, the gage length of the sample may interfere with the actual tensile test in that the tensile tester has a much shorter length in which to get to a desired speed such that a desired strain rate can be achieved.

Consequently, it would be beneficial to provide an apparatus and a method for testing new materials which could eliminate the need to test materials in a ring rolling process. In addition, it would be beneficial to provide an apparatus and a method for testing new materials at strain rates which are similar to those provided by ring rolling processes. Also, it would be beneficial to provide an apparatus and a method, for testing new materials, which are capable of utilizing gauge lengths which are similar to those found in ring rolling processes.

SUMMARY OF THE INVENTION

The present invention reduces the need for placing new materials into a high speed ring rolling process by providing a ring rolling simulation apparatus and method for testing new materials. The method for simulating a ring rolling process and thereby inducing strain on a workpiece comprises the steps of providing a testing apparatus having a first set of teeth and a second set of teeth. The first set of teeth are in communication with at least one load cell, and the second set of teeth are disposed on a movable carriage. A workpiece is disposed adjacent to either the first or the second set of teeth.

The carriage is moved in accordance with a commanded position by time profile thereby linearly engaging the first set of teeth with the second set of teeth. The carriage may also be moved such that the second set of teeth linearly disengage the first set of teeth.

DETAILED DESCRIPTION OF THE INVENTION

Apparatus:

An apparatus that can simulate strain rates similar to those seen on various high speed processes, particularly high speed ring rolling, is provided herein. Thus, the compatibility of the new material with the high speed ring rolling process can be determined via the simulation on the apparatus described herein. Accordingly, the need to incorporate new materials into the high speed ring rolling process for testing is minimized.

Figure 1:
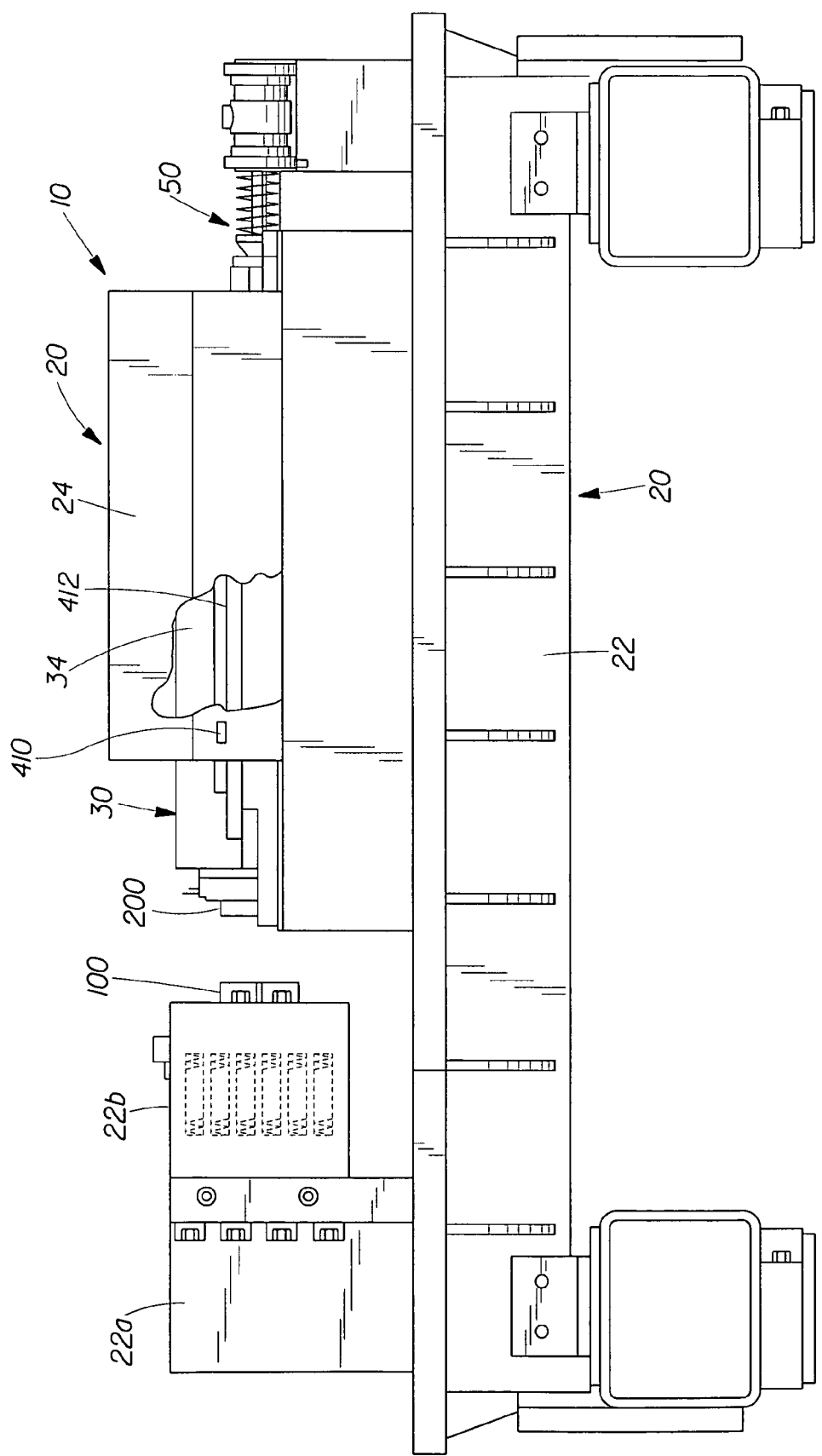
FIG. 1 is a side cutaway view of an apparatus of the present invention which functions to simulate a ring rolling rolls process on a workpiece.

Apparatus 10 comprises a fixed main body 20 comprising a lower portion 22 and an upper portion 24 fixedly coupled to the lower portion 22 as shown in FIG. 1. The apparatus 10 further comprises a linearly reciprocating carriage 30 including a main body portion 34 positioned within a cavity defined by the lower and upper portions 22 and 24 of the main body 20. The apparatus 10 further comprises a generally stationary, substantially planar first plate 100, and a linearly movable, substantially planar second plate 200.

A sensor strip 412 can be affixed to the carriage 30 such that a linear encoder read head 410 can read the sensor strip 412 such that the position of the carriage can be determined. The linear encoder read head 410 can be affixed to the upper portion 24 of the main body 20 in order to facilitate the reading of the sensor strip 412. The linear encoder read head 410 provides a carriage location signal to a drive controller.

The drive controller provides a position signal to at least one linear servo motor or other suitable means for driving the carriage 30. The position signal indicates to the at least one linear servo motor the position of the carriage 30 at various instances in time. Thus, at a certain instance in time, the at least one linear servo motor should place the carriage 30 at a position commanded by the drive controller (referred to hereinafter as the "commanded position"). Therefore, the drive controller provides the commanded position for the carriage 30 which varies by time thereby creating a profile of the commanded position for the carriage by time. The commanded position by time profile of the carriage 30 is further described in U.S. application Ser. No. 10/377,070, entitled "Ring Rolling Simulation Press" filed on Feb. 28, 2003.

In a particular embodiment, the position of the carriage 30 relative to the fixed main body is sensed via the linear encoder read head 410. The linear encoder read head 410 provides feedback as to an actual position of the carriage 30 with regard to the commanded position. Therefore, a difference between the commanded position of the carriage 30 at a specific time versus the actual position of the carriage 30 at that specific time can be calculated. In order to maintain the difference between the commanded position and the actual position of the carriage within about +/−35 micrometers, the apparatus has certain limitations. The carriage 30 can move at a velocity of up to about +/−3 meters/second, and at an acceleration rate up to about +/−196 m/s². Moreover, maintaining the difference mentioned above, a plurality of motors (not shown) can be used so that the carriage 30 can generate a loading force, i.e., the force applied by the second plate 200 against the workpiece and the first plate 100, of up to about +/−20,000 Newtons. Note that if the difference were increased, then the values for the carriage velocity, acceleration, etc. could similarly increase. Different drive controllers or other electrical components could possibly allow the same difference between the commanded position of the carriage 30 versus the actual position of the carriage 30 mentioned above with increased values for velocity, acceleration, etc.

The apparatus 10, constructed in accordance with the present invention, functions to replicate work performed by a pair of ring rolling rolls on a web material. Exemplary ring rolling processes are further described in U.S. Pat. Nos. 4,116892, 4,834,741, 5,143,679, 5,156,793, 5,167,897, 5,422,172, and 5,518,801.

Figure 2A:
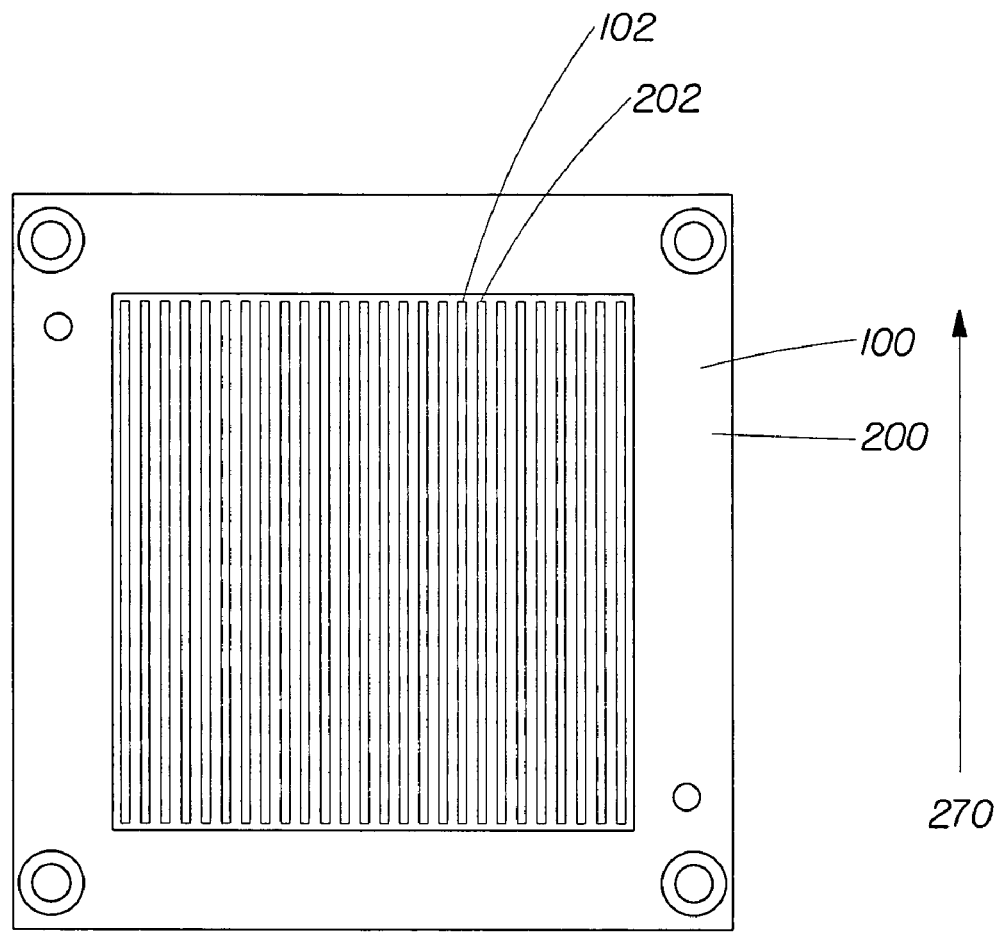
FIG. 2A is a top view of a first plate and a second plate of the apparatus of FIG. 1.
Figure 2B:
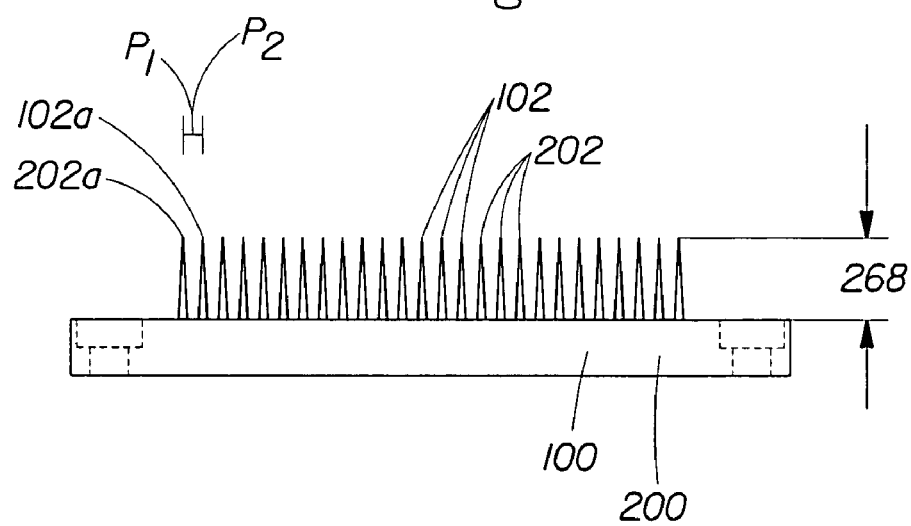
FIG. 2B is a side view of the first and second plate of the apparatus of FIG. 1.

To accomplish the simulation of the ring rolling process, both the first plate 100 and the second plate 200 can be equipped with teeth as shown in FIGS. 2A and 2B. The first plate 100 can be equipped with first teeth 102 spaced apart at a first pitch $p_1$ and the second plate 200 can be provided with second teeth 202 spaced apart at a second pitch $p_2$. In the FIGS. 2A and 2B, the first and second pitches $p_1$ and $p_2$ are equal to one another.

In addition, the carriage should also be able to reciprocate thereby allowing the second teeth 202 on the second plate 200, which is fixed to the carriage, to engage the first teeth 102 and disengage the first teeth 102. Furthermore, the first plate 100 and the second plate 200 should be aligned such that the first teeth 102 and the second teeth 202 are offset thereby allowing the first teeth 102 and the second teeth 202 to engage one another. Also, because the first teeth 102 and the second teeth 202 are adaptable to engage one another, the pitches of both sets of teeth, i.e. $p_1$ and $p_2$, in certain preferred embodiments, should either be equal or should be a multiple of the other. Dissimilar pitches, excluding the instance where one pitch is a multiple of the other, can preclude the second teeth 202 from being able to fully engage the first teeth 102 (see FIGS. 8C and 9A for illustrations of fully engaged first and second teeth). For this reason, the remainder of the discussion pertaining to the apparatus and method will assume that the pitch for the first teeth 102 is equal to the pitch of the second teeth 202. In a suitable embodiment, both the first teeth 102 and the second teeth 202 may be fixed to the apparatus such that when the second teeth 202 are engaged with the first teeth 102, first teeth 102 and the second teeth 202 are substantially parallel to one another.

Figure 2C:
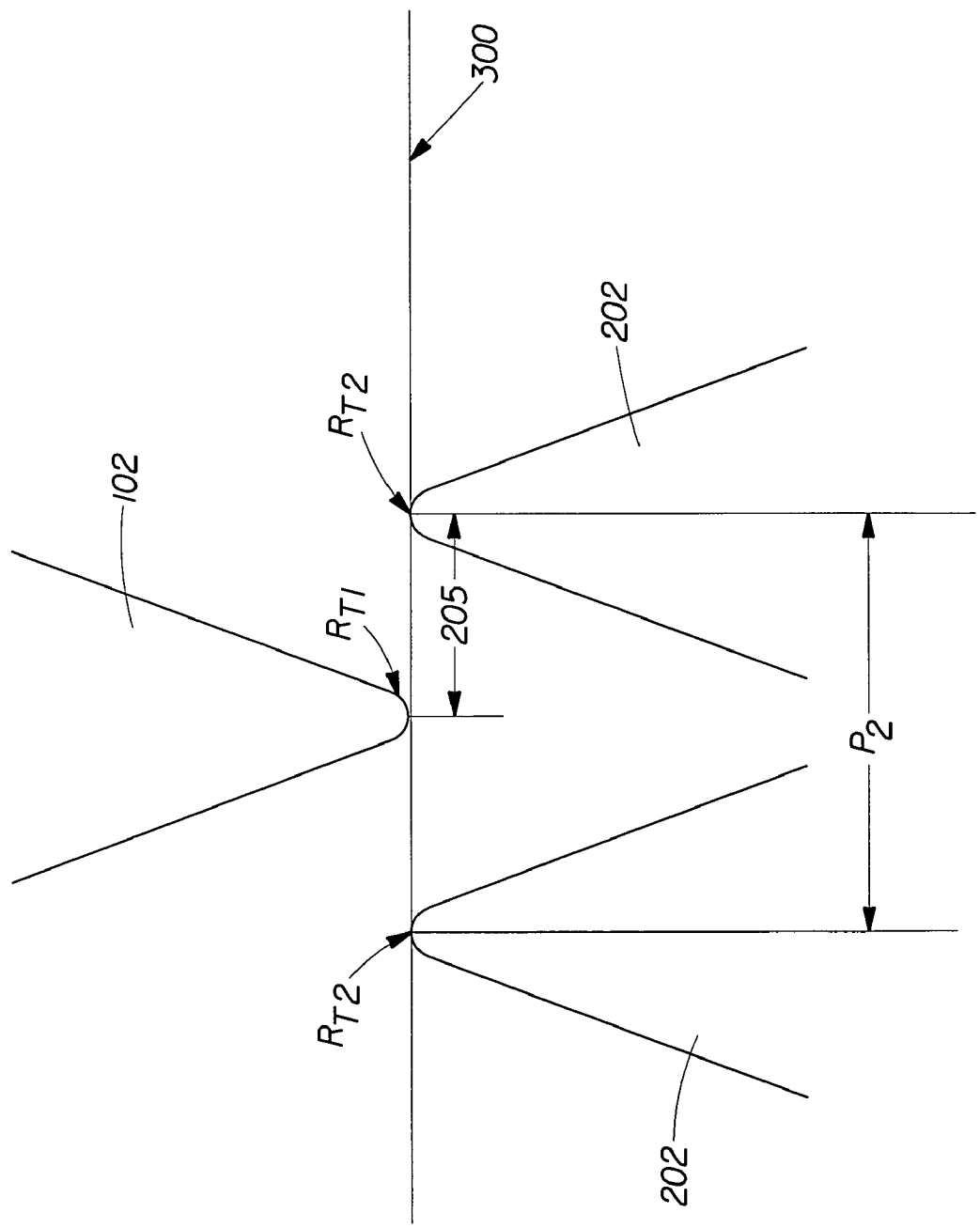
FIG. 2C is a close up view of a first tooth and a plurality of second teeth from the first plate and the second plate of FIG. 2B.

The teeth pitches, tooth height, and tooth tip radius may vary greatly. The ranges below are provided merely as examples of these parameters for the first or second teeth currently used. The pitches of either the first teeth 102 or the second teeth 202 currently used range from about 0.75 mm to about 5.10 mm. A height 268 of either the first teeth or second teeth ranges from 1.50 mm to about 25.0 mm. A tip radius of the first or second teeth ranges from 0.10 mm to 0.13 mm as shown in FIG. 2C denoted by $R_{T1}$ and $R_{T2}$.

The range of teeth pitches of the first teeth 102 and the second teeth 202 provide a wide range of gage lengths also. As shown in FIG. 2C, the gage length 205 of the workpiece 300 is equal to the pitch, either $p_1$ or $p_2$ divided by two. Thus, a smaller pitch yields a smaller gage length of the workpiece 300. Based on the current pitch range used, the gage length of the workpiece 300 ranges from about 0.375 mm to about 2.55 mm.

Figure 3A:
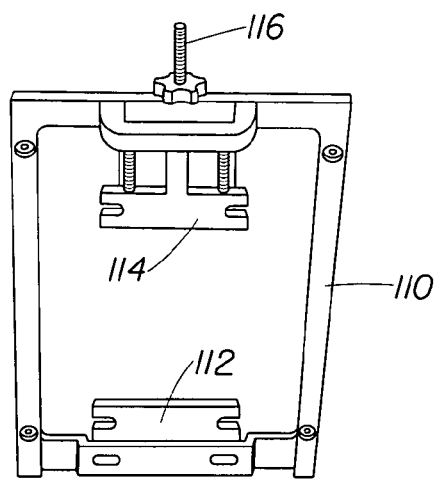
FIG. 3A is a perspective view of a workpiece holder.
Figure 3B:
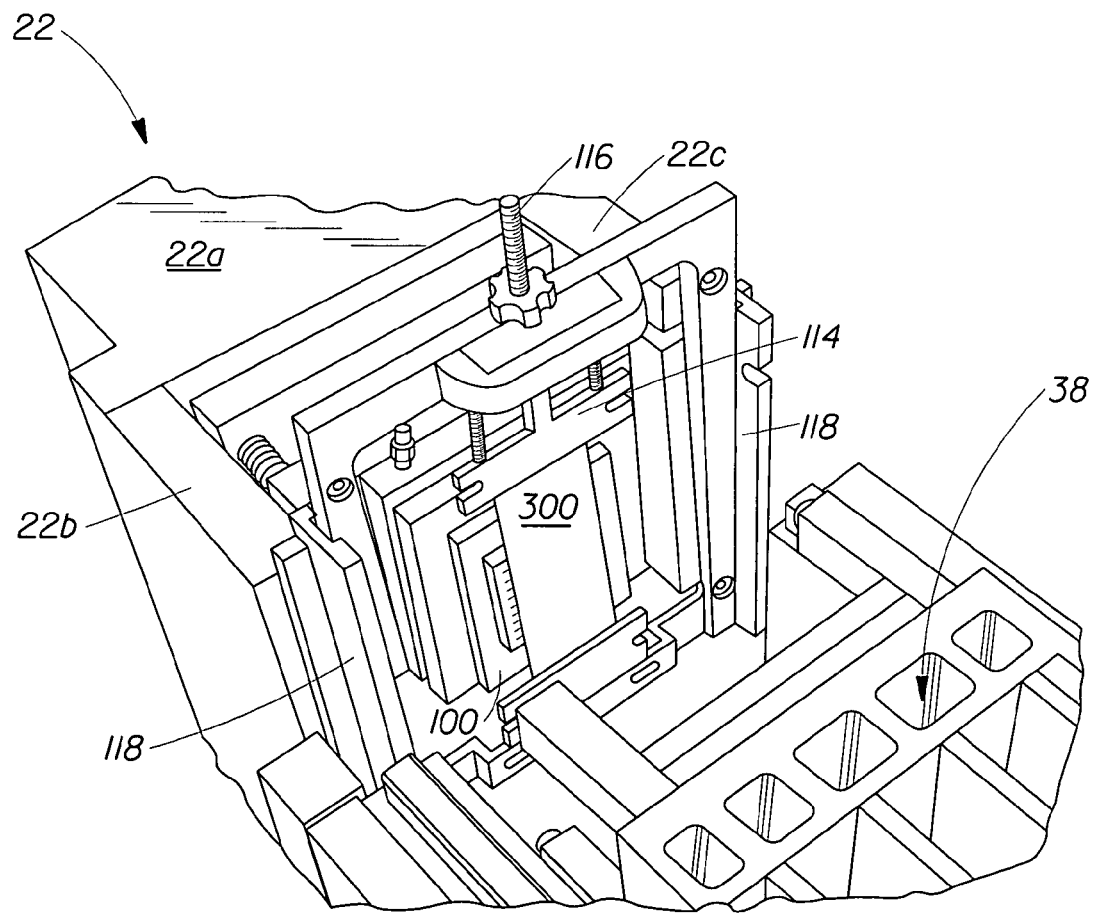
FIG. 3B is a perspective view of the workpiece holder illustrated in FIG. 3A mounted in first and second receiving members which, in turn, are fixedly mounted to a lower main body portion of the apparatus in FIG. 1.

A holder 110 can be mounted on first and second receiving members 118, which, in turn, are fixedly mounted to the lower portion 22 of the apparatus as shown in FIGS. 3A–3B. The holder 110 can be disposed proximate to the first plate 100. The holder 110 may comprise a stationary mounting member 112 and a movable mounting member 114. Once a workpiece 300 is mounted to or gripped by the mounting members 112 and 114, the movable member 114 may be moved via a screw 116 or other mechanism such that a desired tension may be applied to the workpiece 300. Preferably, the workpiece 300 is tautly mounted in the holder 110 such that when the second teeth engage the first teeth, the workpiece 300 actually experiences strain rather than simply displacement with respect to the first set of teeth or second set of teeth depending on where the holder 110 is mounted. However, the workpiece 300 should be mounted in the holder 110 such that the workpiece 300 is not prematurely strained, i.e. prior to the second teeth engaging the first teeth. The holder 110 can optionally be mounted to the carriage 30 such that the workpiece 300 is disposed proximate to the second plate.

Figure 4:
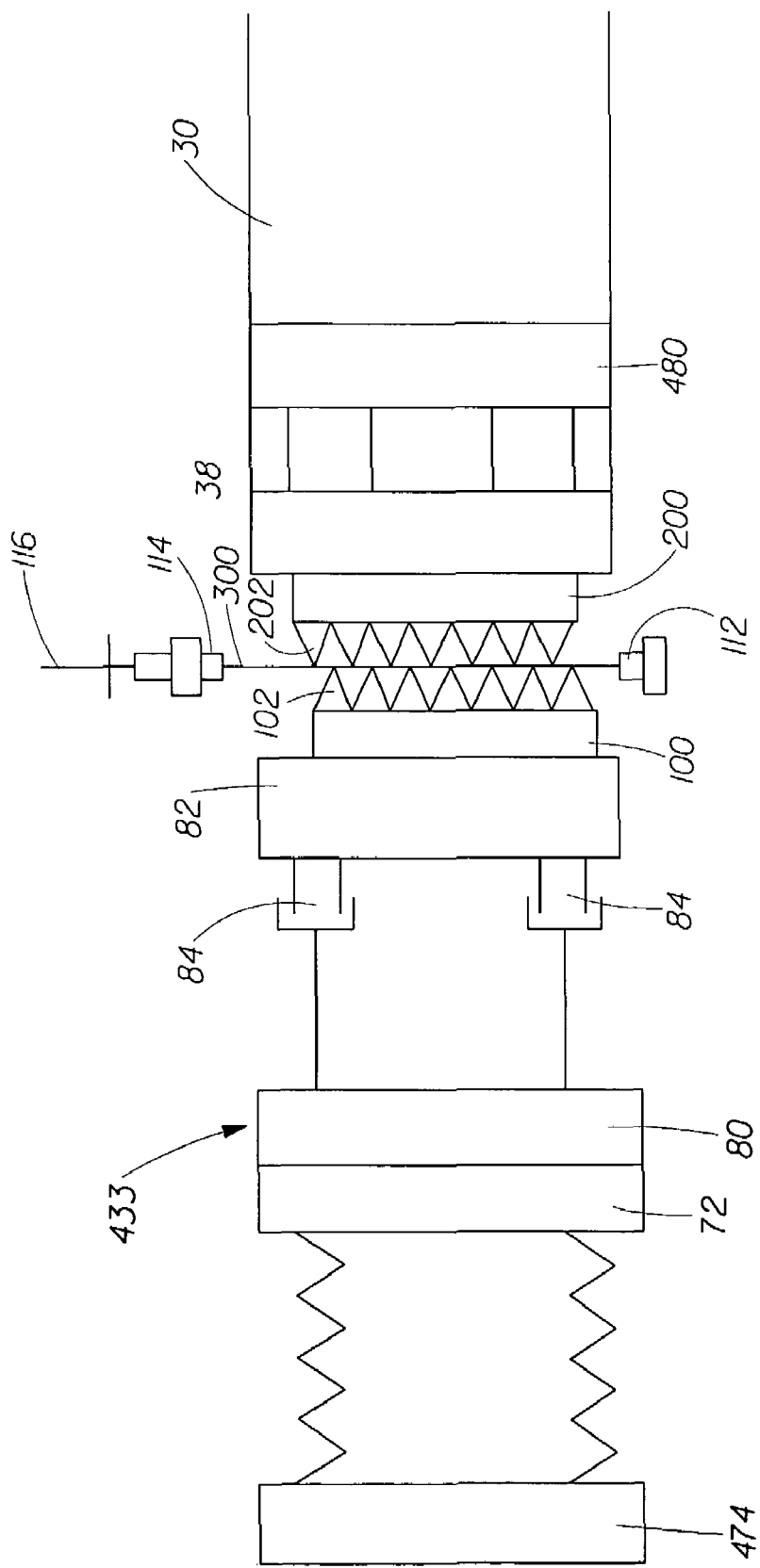
FIG. 4 is a schematic view of a carriage side and a load side of the apparatus of FIG. 1.

Prior to engaging a workpiece 300 with the plates 100 and 200, the workpiece 300 may be heated to a predefined temperature by moving the carriage 30 to a position such that the second teeth 202 on the second plate 200 are positioned just adjacent to the workpiece 300 as shown in FIG. 4. A heater controller may maintain the heated plates 38 and 82 at the predefined temperature. The workpiece 300 can be heated to a desired temperature by maintaining the workpiece 300 between the first and second plates 100 and 200 until the workpiece reaches the predefined temperature. Note that the heater controller may also maintain the heated plates 38 and 82 at above the predefined temperatures such that the workpiece reaches the predefined temperature in a shorter length of time. The temperature ranges possible are from ambient to 150° C.; however, typically, the workpieces are not heated over 100° C.

When the second teeth 202 engage the first teeth 102, a load is experienced both by the workpiece 300 and by the load sensing side 433 of the apparatus described above. The load cells 84 can be positioned between a cooled plate 80 and the heated plate 82. The load cells 84 can provide a load signal to the drive controller mentioned above.

The movement of the linearly reciprocating carriage is effected by at least one linear servo motor (not shown) or other suitable devices. The apparatus discussed above is further described in U.S. application Ser. No. 10/377,070 entitled, "Ring Rolling Simulation Press" filed on Feb. 28, 2003.

Figure 5:
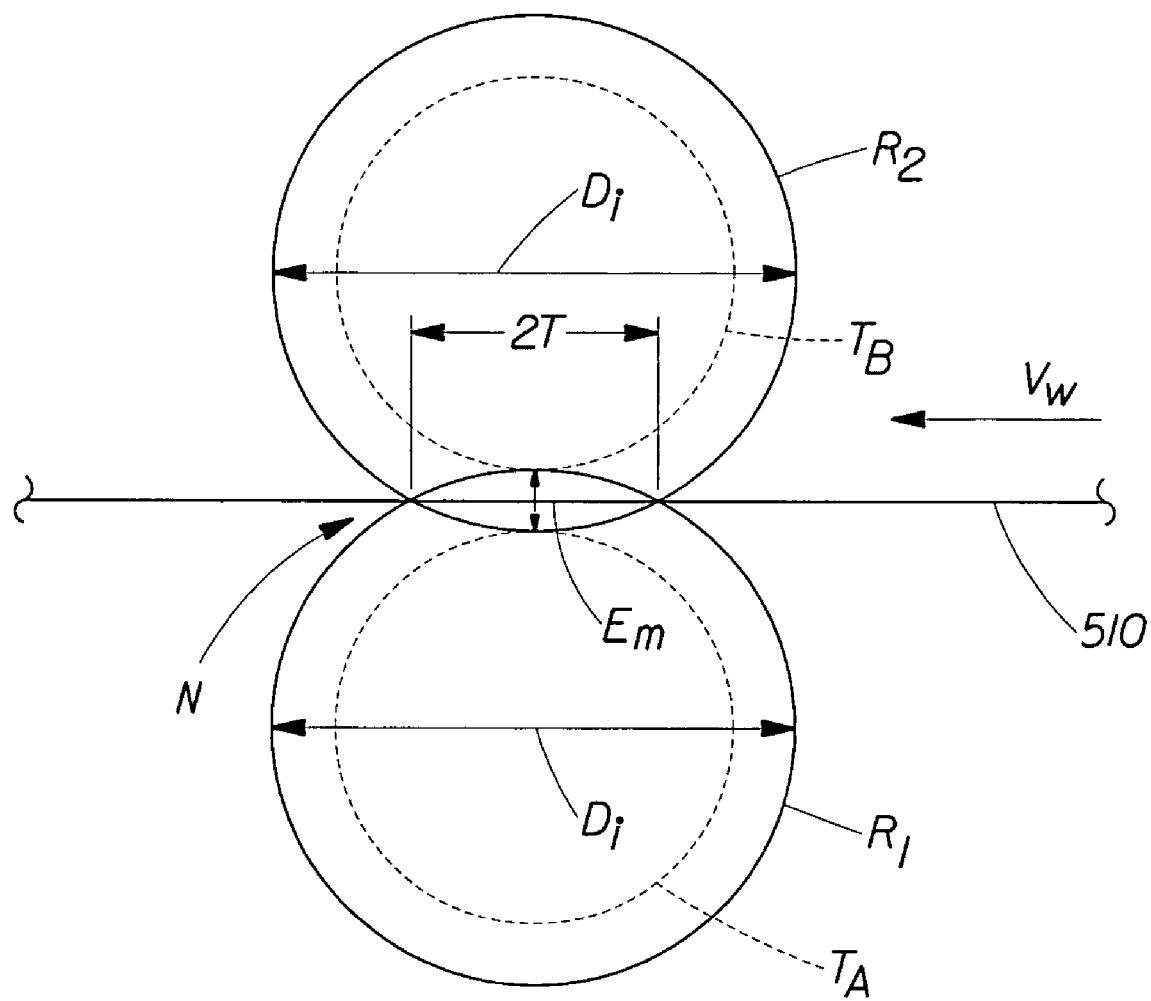
FIG. 5 is a schematic illustration of first and second teeth on first and second rolls engaging during a ring rolling operation.

Methodology/Operation of Apparatus:

Prior to running the simulation, there are many parameters which need to be measured. Many of the parameters are measured from the ring rolling process being simulated. One of the parameters that should be determined is a desired web velocity $V_w$, i.e., the velocity at which the workpiece would run if passed between a pair of ring rolling rolls $R_1$ and $R_2$ in the ring rolling process (see FIG. 5). In addition, a maximum depth of engagement $E_M$ of the first and second teeth $T_A$ and $T_B$ on the ring rolling rolls $R_1$ and $R_2$; the pitch p of the first and second teeth $T_A$ and $T_B$ on the first and second rolls $R_1$ and $R_2$; and the diameter Di of the first and second rolls $R_1$ and $R_2$ should be determined as well. Alternatively, the simulation can be defined with the knowledge of variables such as maximum strain and maximum strain rate if the tip radius, teeth pitch, and E(t) are also determined. The equations for strain are provided hereinafter.

In the ring rolling process, the first teeth $T_A$ on a first roll $R_1$ engage with second teeth $T_B$ on a second roll $R_2$. As shown, a given point on a web material 510 moving at a web velocity $V_w$ is engaged by the first and second teeth $T_A$ and $T_B$ for a time period 2T as it moves through the nip N defined by the first and second rolls $R_1$ and $R_2$. The equations pertaining to T, i.e. one half of 2T, E(t) (the depth of engagement with respect to time), $V_e$ (the engagement rate of change or tooth tip velocity), and $A_e$ (the tooth tip acceleration) are further discussed in U.S. application Ser. No. 10/377,070, entitled "Ring Rolling Simulation Press" filed on Feb. 28, 2003.

Note that all of the equations, either herein or incorporated by reference, are based on an assumption that the diameter $D_i$ of roll $R_1$ is equal to the diameter $D_i$ of roll $R_2$. Where the diameters of the rolls $R_1$ and $R_2$ differ, the simulation process described herein remains the same with the exception that the equations corresponding to the variables mentioned above must be re-derived taking into account the difference in roll diameters.

Figure 6:
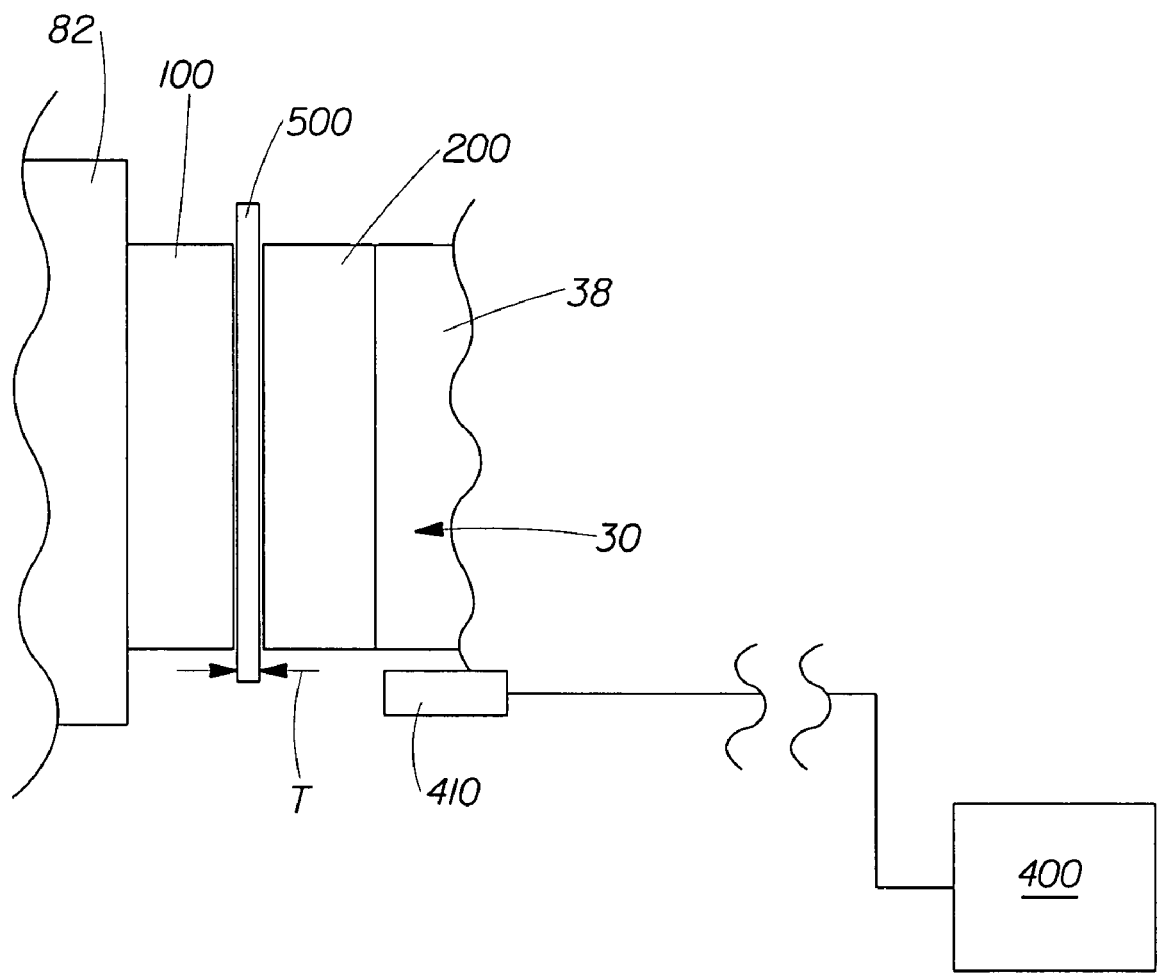
FIG. 6 is a side view of a calibration plate being engaged by the first and second plates of the apparatus of FIG. 1.

Optionally, prior to conducting a simulation, the apparatus can be calibrated. The calibration procedure may be performed as exemplified below. A calibration plate 500, having a known thickness T, can be positioned adjacent to the first plate 100, as shown in FIG. 6. The drive controller 400 output to the at least one linear servo motor can be modified such that the peak force capable of being provided by the at least one linear servo motor is substantially reduced. As an example, during calibration, the drive controller 400 can limit the at least one linear servo motor to approximately 2% of maximum force that the at least one linear servo motor can produce. The drive controller 400 can furthermore control the movement of the second plate 200 so that it slowly moves toward the first plate 100 until it engages the calibration plate 500. At the point of engagement, a position error of the at least one linear servo motor increases because movement of the carriage 30 is blocked by the calibration plate 500. The position signals generated by a linear encoder read head 410, which are provided to the drive controller, alert the drive controller 400 that the position of the carriage 30 is not changing even though the drive controller 400 is generating a drive signal to provide power to the at least one linear servo motor. Thus, the increase in position error is detected by the drive controller 400.

Figure 8A:
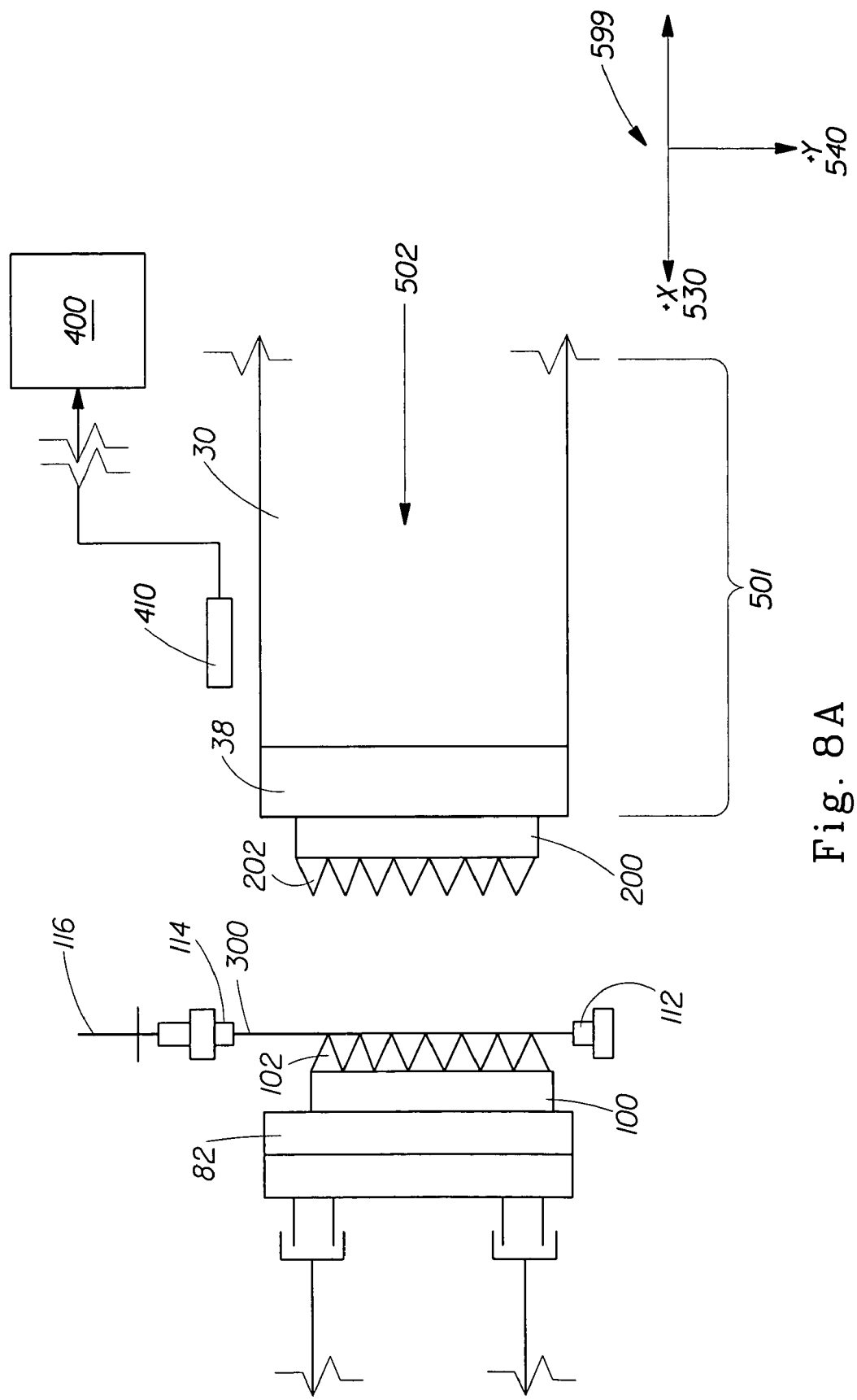
FIGS. 8A–8C are schematic views of the carriage and the load side of the apparatus of FIG. 1 depicting the carriage moving in a forward direction.
Figure 8B:
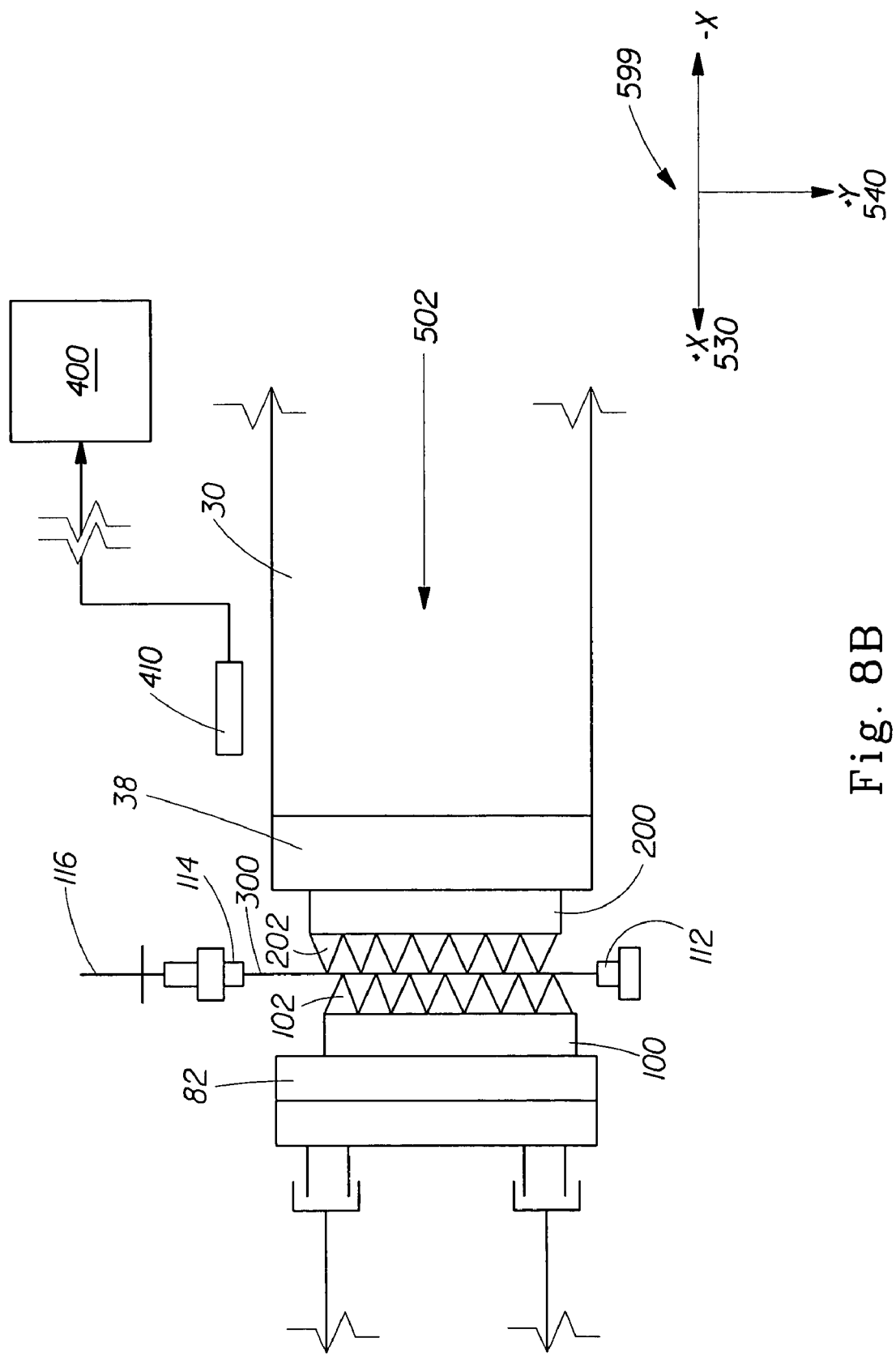

In response to an increase in position error of the carriage 30, the drive controller 400 receives carriage position signal from the linear encoder read head 410 that the carriage 30 is positioned a distance equal to the thickness of the calibration plate 500 away from a "0 position." For the carriage 30, the "0 position" is the position of the carriage 30 just as the second teeth 202 on the second plate 200 cross a plane separating the teeth 102 and 202 on the first and second plates 100 and 200, respectively (see FIG. 8B for illustration of the "0 position"). The drive controller 400 defines the current position of the carriage 30 as being a distance away from the "0 position" equal to the thickness of the calibration plate 500 which is then verified by the position signal from the linear encoder read head 410.

Figure 7:
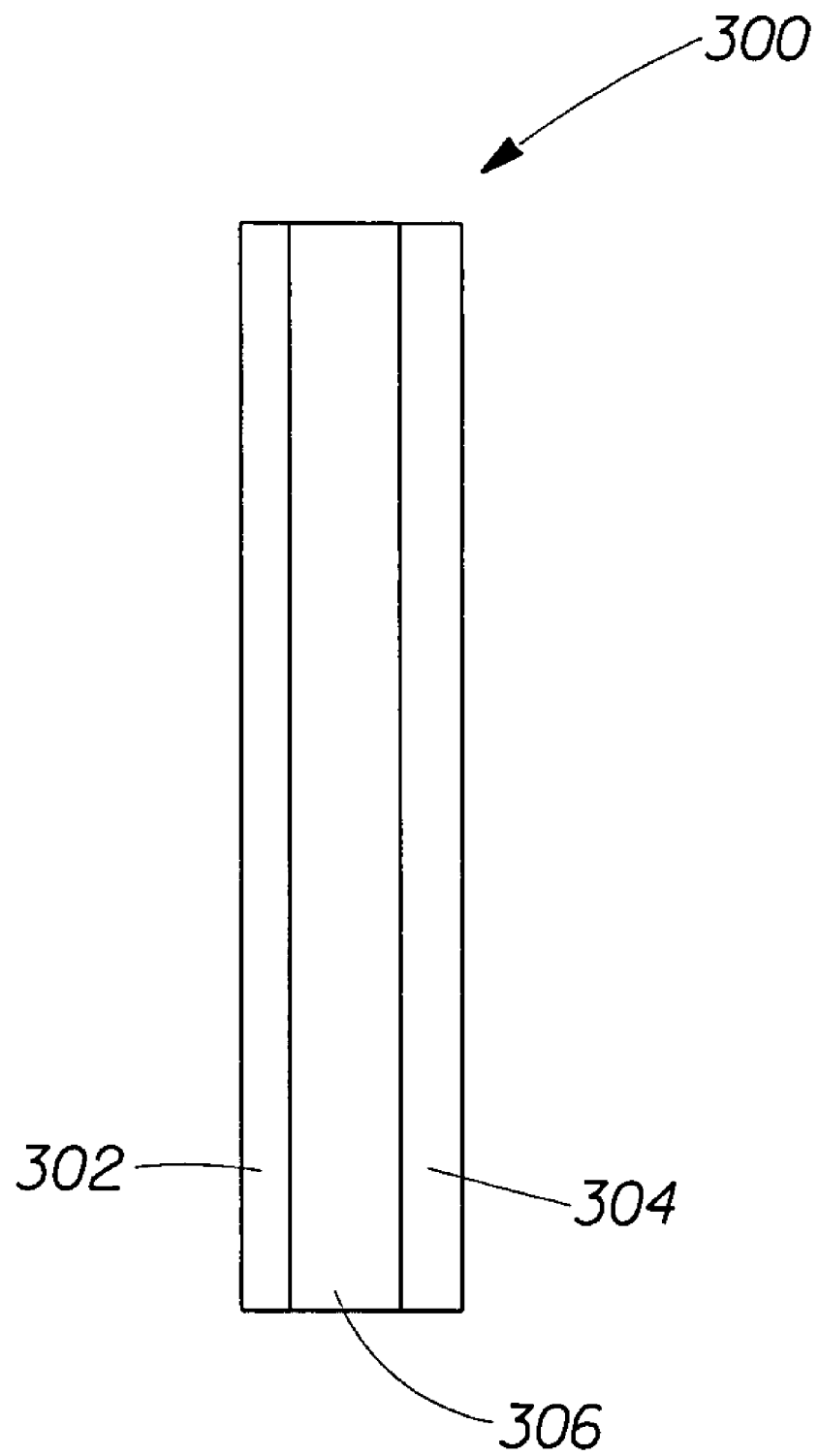
FIG. 7 is an elevation view of a workpiece comprising a laminate structure.

Another consideration, before beginning a simulation is the type of workpiece that will be tested. The workpiece 300 may range from wovens, nonwovens, fabrics, films, adhesives, or combinations thereof. Moreover, the workpiece 300 may comprise a laminate structure as shown in FIG. 7. For example, for the testing of adhesives, the workpiece 300 may comprise a laminate structure comprising a first substrate 302, a second substrate 304, and an adhesive film layer 306 disposed between the first substrate 302 and the second substrate 304.

Note that if a laminate, as described in the above example, is desired such that an adhesive can be tested, then the first substrate 302 and the second substrate 304 may be selected such that they fail before the adhesive does. Alternatively, if the laminate itself is desired such that the laminate can be tested, the first and second substrates 302, 304 may be selected such that they interact heavily with the adhesive and do not fail before the adhesive. An example of a laminate structure for adequately testing an adhesive where the substrates fail before the adhesive comprises a tissue as both the first substrate 302 and the second substrate 304. Suitable tissue is sold under the trade name Puffs and manufactured by The Procter and Gamble Company located in Cincinnati, Ohio.

In order to simulate a ring rolling process, the carriage should be capable of linearly reciprocating in both a forward direction and a reverse direction. The movement of the carriage in the forward direction causes the engagement between the first teeth and the second teeth thereby simulating a portion of the ring rolling operation (discussed hereinafter with regard to FIGS. 8A–8C). In contrast, the movement of the carriage in the reverse direction causes the first teeth and the second teeth to disengage (discussed hereinafter with regard to FIGS. 9A–9C).

As an example of the operation of the apparatus during a simulation, the movement of the carriage in the forward direction and the reverse direction can be broken up into eight segments. The forward direction can be separated into four discrete segments: a forward acceleration segment; a forward linear segment; a forward transition segment; and an engagement segment. In addition, the carriage should also move in a reverse direction from the position where the second teeth on the second plate are positioned to a desired depth relative to the first teeth on the first plate back to its home position. This carriage movement in the reverse direction can be similarly separated into four discrete segments: a disengagement segment; a reverse transition segment; a reverse linear segment; and a reverse acceleration segment. Note that in order to simulate the ring rolling process, it is not necessary to split the movement of the carriage into eight segments. Any number of segments can be used; however, the carriage at engagement should be traveling at such a velocity that a desired carriage position by time profile is achieved.

In the exemplary simulation, the beginning of a segment, excluding the forward acceleration segment, is concurrent in time with the ending of a preceding segment. Each of the eight segments may comprise a plurality of equal discrete time intervals. Note, that this does not imply that each segment has an equal number of discrete time intervals. The total time period required for execution of the eight segments can be determined and then divided by a predefined number of control points. The predefined number of control points are governed by the number of points that the drive controller is capable of processing during a ring rolling simulation. For example, if the drive controller can process 7990 control points, the total time period to perform the eight segments is divided by the number of control points. As an example to demonstrate the calculation of the time of each discrete time interval, if the total time period required for execution of the eight segments was 2.79 seconds, then each discrete time interval would be roughly 350 microseconds. As another example, if the total time period required for execution of the eight segments was 1.79 seconds, then each discrete time interval would be roughly 224 microseconds. However, depending on the capability of the drive controller 400, the discrete time intervals may be limited in size. For example, a minimum value for a discrete time interval may be set at 300 microseconds. If the calculated value for the discrete time intervals is less than the minimum value for the discrete time interval, the minimum value is used. If the minimum value is used, then the number of control points is reduced. With a different drive controller, the minimum value for the discrete time intervals may be lowered, and the number of control points may increase.

During the forward acceleration segment, the carriage 30 moves in the first direction 502 along an x-axis from a starting position 501 as shown in FIG. 8A. In the forward acceleration segment, the carriage 30 can be accelerated at a constant rate from a zero velocity to a positive velocity. The positive velocity (the carriage 30 is moving in the forward direction 502, which corresponds to the positive x direction 530) is equal to the initial velocity of the forward linear segment. The carriage home position 501 is defined by an engineer/technician and is relative to a carriage "0 position." Typically, it is equal to or nearly equal to the maximum distance the carriage 30 may be positioned away from its "0 position." The distance for this segment is equal to the distance the home position is spaced from the carriage "0 position" minus the distances the carriage 30 moves during the forward linear and forward transition segments. The time for forward acceleration segment can be predefined.

During the forward linear segment, the tooth tip acceleration (corresponds to the carriage acceleration) can decrease to zero such that the tooth tip velocity can be maintained at a constant value. The time period for this segment can be set to a predefined value, e.g., 2.0 milliseconds, and typically the same time period can be used for this segment during all ring rolling process simulations. The final tooth tip acceleration within this segment can be equal to zero and the final tooth tip velocity should equal the initial tooth tip velocity for the forward transition segment.

The total time period for the forward transition segment can be set to a predefined value, e.g., 3.1 milliseconds and, typically, the same time period can be used for this segment during all ring rolling process simulations. The final tooth tip position (corresponds to a final carriage position relative to the carriage "0 position"), final tooth tip velocity, and final tooth tip acceleration for this segment are all equal to the initial tooth tip position, initial tooth tip velocity and initial tooth tip acceleration for the engagement segment. Further, the initial tooth tip acceleration for this segment can be 0. From these given values, a processor memory unit determines initial and intermediate tooth tip positions, initial and intermediate tooth tip velocity values, and initial and intermediate tooth tip acceleration values for this segment.

Figure 8C:
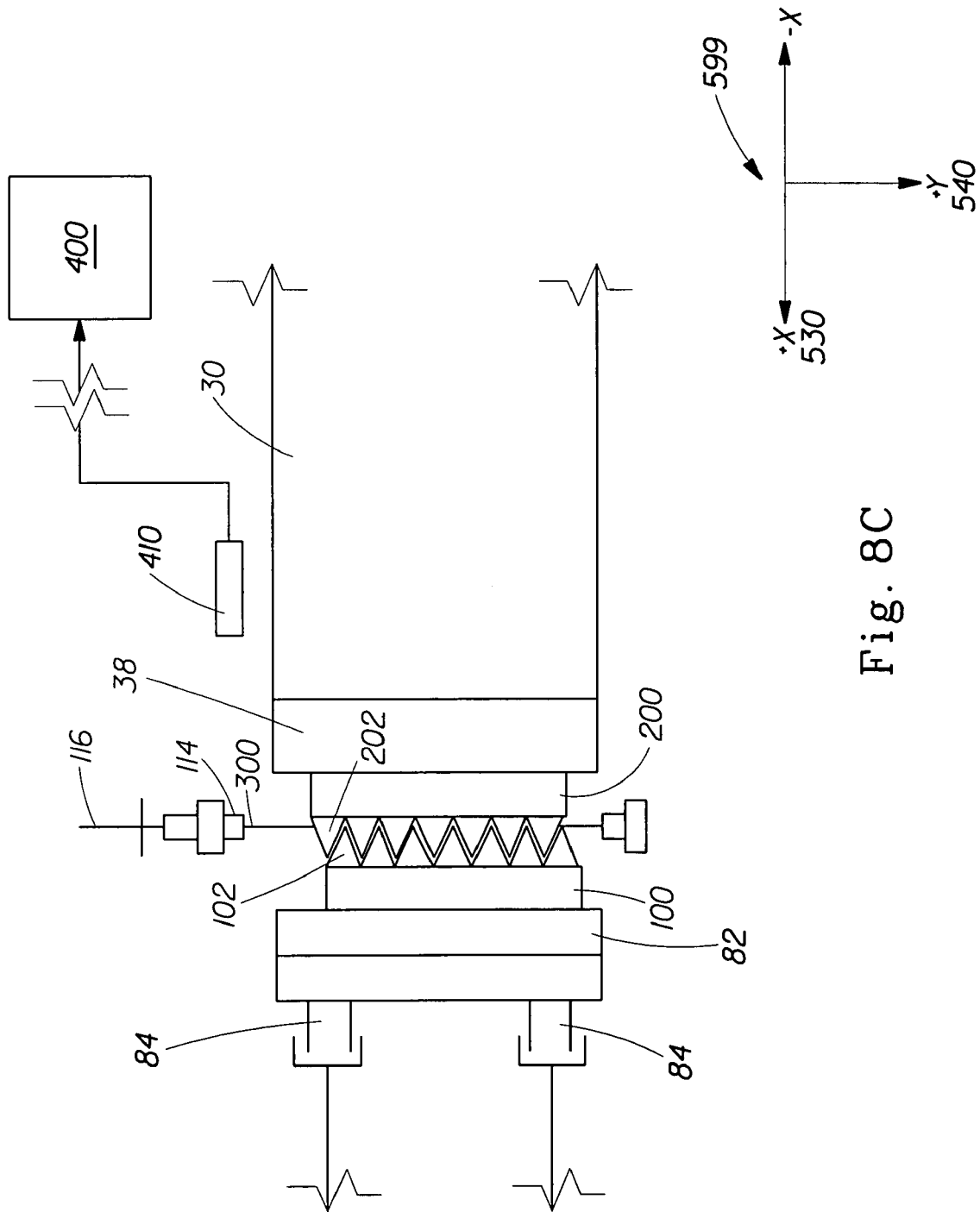

The engagement segment has a defined beginning and ending time. The beginning of the engagement segment is defined as occurring just after the carriage 30 has reached its "0 position," i.e., the position of the carriage 30 just as the second teeth 202 cross a plane separating the first and second teeth 102 and 202 as shown in FIG. 8B. Once the carriage 30 reaches its "0 position," the drive controller 400 causes the at least one linear servo motor to continue to drive the carriage 30 toward the first plate 100 such that the first and second plates 100 and 200 engage the workpiece 300. Furthermore, the at least one linear servo motor continues to drive the carriage 30 such that the second teeth 202 on the second plate 200 move to a desired engagement depth $E_M$ relative to the first teeth 102 on the first plate 100 as shown in FIG. 8C. The engagement segment ends just after the second teeth 202 on the second plate 200 are positioned at a desired depth $E_M$ relative to the first teeth 102 on the first plate 100. The movement of the carriage 30 during this segment is defined by the equation of E(t).

Figure 9A:
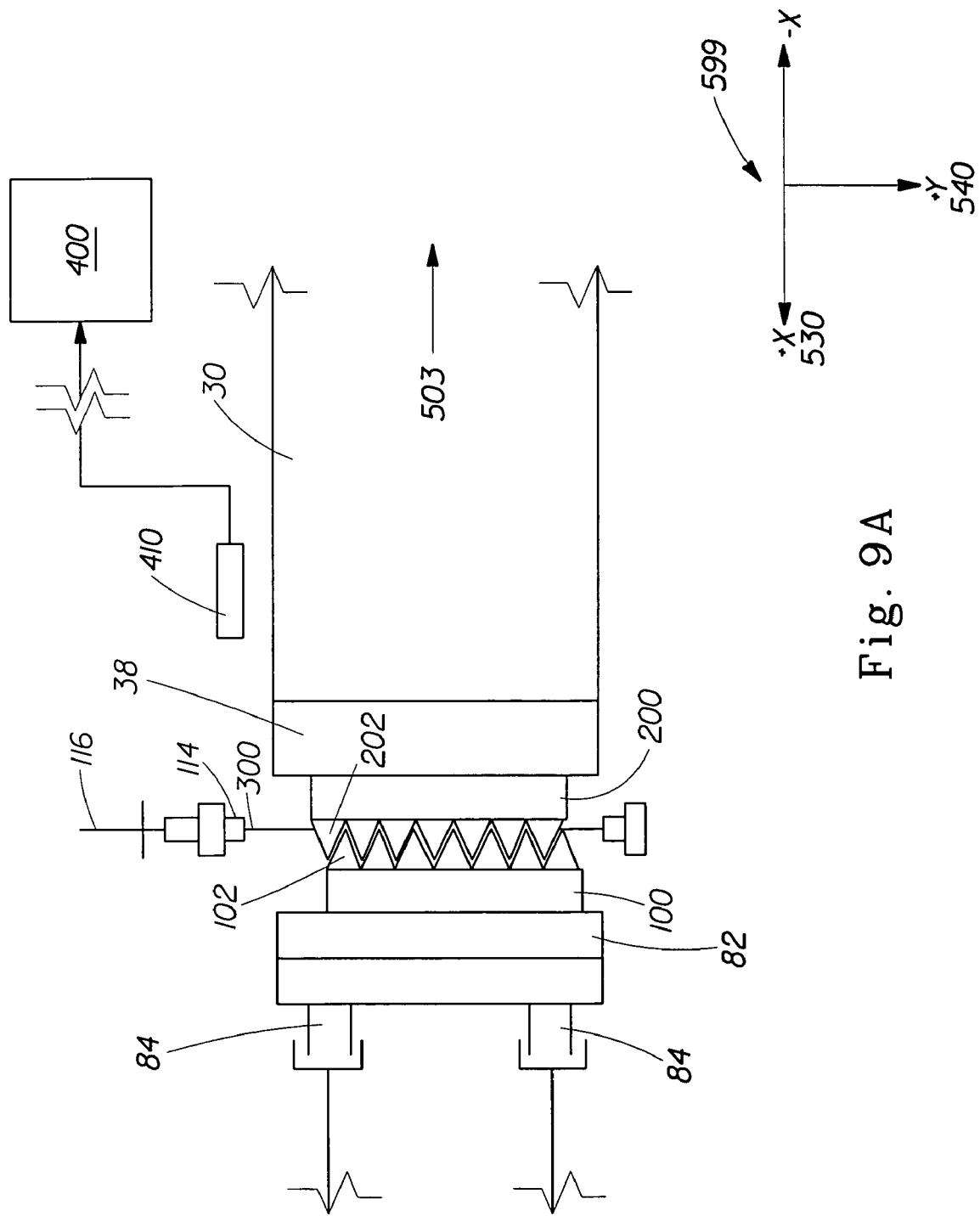
FIGS. 9A–9C are schematic views of the carriage and the load side of the apparatus of FIG. 1 depicting the carriage moving in a reverse direction.
Figure 9B:
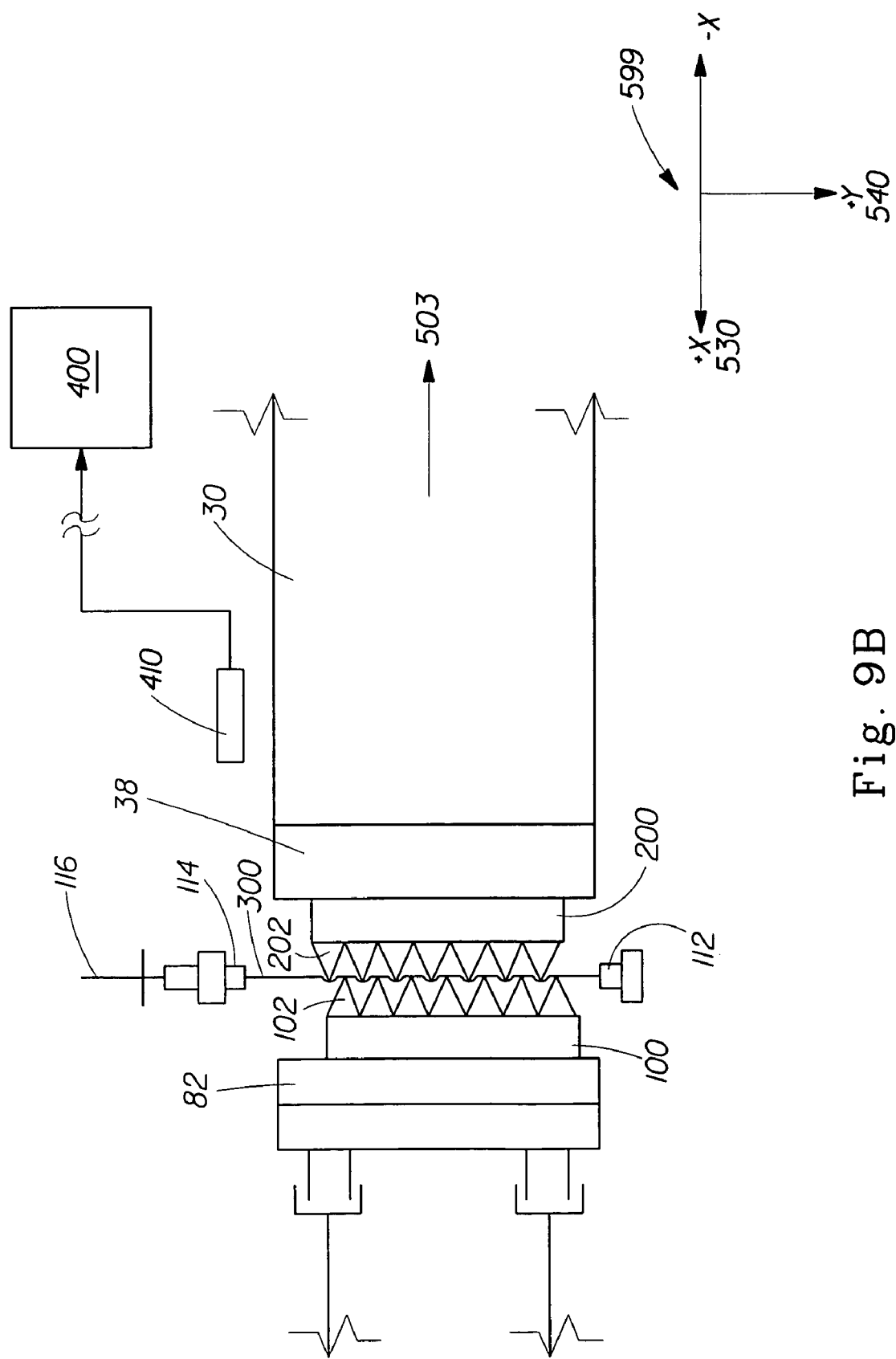

The disengagement section begins with the ending of the engagement segment which is defined as occurring just after the second teeth 202 on the second plate 200 are positioned at a desired depth $E_M$ relative to the first teeth 102 on the first plate 100 (see FIG. 9A). The carriage 30 moves in the second direction 503 such that the second plate 200 returns to the "0 position" as shown in FIG. 9B. Similar to the engagement segment, the movement of the carriage is defined by the equation E(t).

During the engagement and disengagement segments of the simulation, the apparatus of the present invention is capable of producing very high strain rates on a workpiece. As an example, the apparatus of the present invention, can induce a strain rate in excess of 500 $s^{-1}$. The apparatus, as currently used, can induce strain rates on a workpiece which range from about 1 $s^{-1}$ to about 2245 $s^{-1}$. Note that the strain rate is a function of many variables, therefore, strain rates in excess of 2245 $s^{-1}$ may be obtainable. The equations for determining strain rate are discussed hereinafter.

The total time period for the reverse transition segment can be set to a predefined value, e.g., 3.1 milliseconds and, typically, the same time period is used for this segment during all ring rolling process simulations. The initial tooth tip position, initial tooth tip velocity, and initial tooth tip acceleration for the reverse transition segment must be equal to the final tooth tip position, final tooth tip velocity and final tooth tip acceleration for the disengagement segment. Further, the final tooth tip acceleration should be 0 at the end of the reverse transition segment. From these given values, the processor/memory unit determines initial and intermediate tooth tip positions, initial and intermediate tooth tip velocity values and initial and intermediate tooth tip acceleration values for this segment.

During the reverse linear segment, the tooth tip acceleration can begin at zero and change to a constant tooth tip deceleration value. The final deceleration value for the reverse linear segment can be the constant tooth tip deceleration value for the reverse acceleration segment discussed below. This segment can be used to buffer any jerking motion of the carriage 30 as it changes from a positive acceleration to a negative acceleration. The time period for this segment can be set to a predefined value, e.g., 2.0 milliseconds, and typically, is the same time period used for this segment during all ring rolling process simulations. The initial tooth tip velocity for this segment should be equal to the final tooth tip velocity for the reverse transition segment.

Figure 9C:
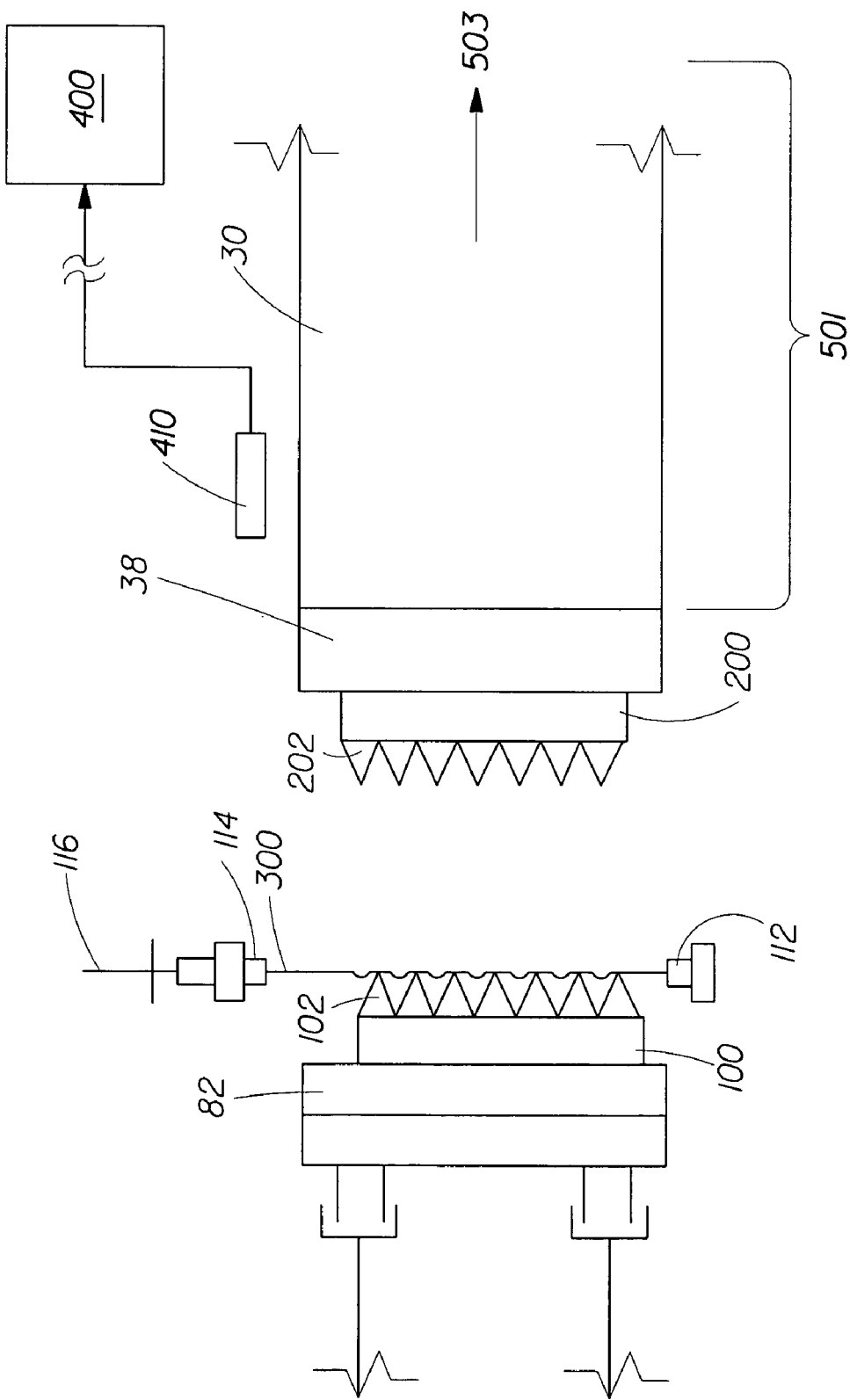

During the reverse acceleration segment, the carriage 30 can decelerate at a constant rate from an initial velocity equal to the final velocity of the Reverse Linear Segment down to a 0 velocity, at which point the carriage is at its home position 501 as shown in FIG. 9C. The distance for this segment is equal to the distance the home position is spaced from the carriage "0 position" minus the distances the carriage 30 moves during the reverse linear and reverse transition segments. The time period for this segment is not necessarily predefined. The processor/memory unit determines a constant rate of deceleration (i.e., a tooth tip deceleration) required for the carriage 30 to be decelerated from a velocity equal to the final tooth tip velocity for the reverse linear segment to a 0 velocity within the calculated distance for this segment.

Figure 10:
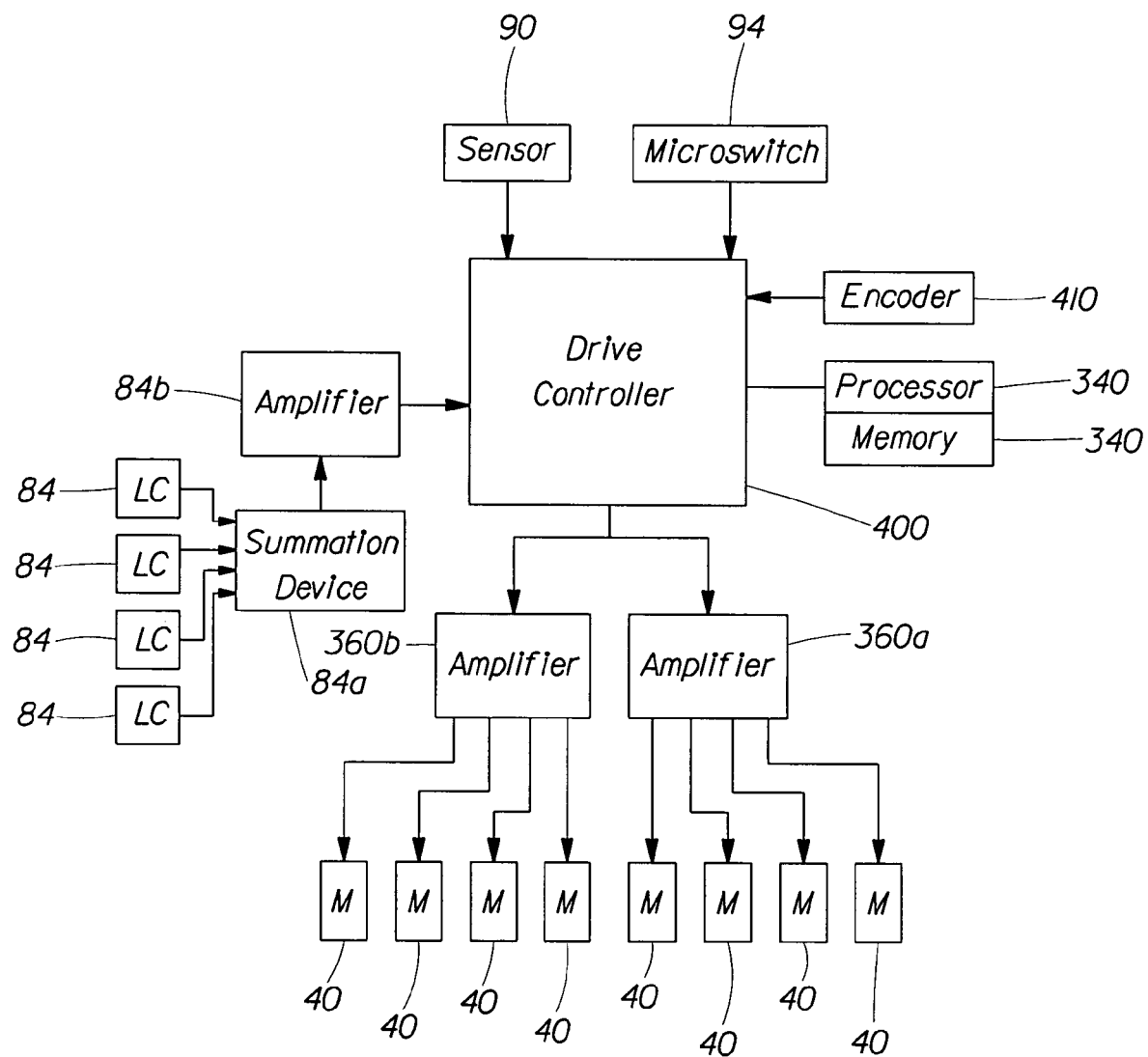
FIG. 10 is a block diagram illustrating a driver controller and amplifiers for controlling the movement of the carriage of FIG. 1.

As mentioned previously, the commanded position of the carriage with respect to time is governed by the drive controller 400 which receives position feedback information from the linear encoder read head 410 as shown in FIG. 10. The drive controller 400 compares the actual position of the carriage determined from the position information provided by the read head 410 to the predefined commanded positions. The drive controller 400 also takes into consideration force information generated by the load cells 84 in order to control the motors.

The load cells 84 measure the load provided by the engagement of the first plate and the second plate with the workpiece. The load cells 84 provide signal to a summation device 84a. The summation device 84a functions to combine the signals generated by the load cells 84 and generate a single force signal to an amplifier 84b. An amplified force signal is generated by the amplifier 84b to a drive controller 400 and is representative of the combined force directly applied to the load cells 84 by the cooled plate. The combined force is a result of the first and second teeth engaging a workpiece as discussed above. Based on the signal from the load cells 84, the drive controller 400 either increases the current to the linear servo motors 40 or decreases the current to the linear servo motors 40 depending on whether the load is increasing or decreasing, respectively.

The information regarding carriage position, time, and load sensed by the load cells 84 is provided by the drive controller 400 to a processor/memory unit 340. The processor/memory unit 340 receives, stores, and processes the data received from the drive controller. Utilizing this data, as well as other parameters which are input into the process/memory unit 340, the processor/memory unit 340 determines various parameters for each discrete time interval. The processor/memory unit 340 determines, for each discrete time interval, an engagement position or tooth tip position (equal to the carriage position from the "0 position"), a tooth tip velocity (which is equal to the carriage velocity), and tooth tip acceleration (which is equal to the carriage acceleration). The equations concerning the parameters mentioned above with respect to each individual discrete time interval are further discussed in U.S. application Ser. No. 10/377,070, entitled "Ring Rolling Simulation Press" filed on Feb. 28, 2003.

The processor/memory unit 340 can also manipulate the data received from the drive controller 400 and calculate from that data such values as strain, the load experienced by the workpiece, a stress, an activation energy, and a residual energy. The manipulation of the data and input of control parameters to the drive controller 400 is via a software program. A suitable software program for manipulating the accumulated data and for the input of control parameters into the drive controller 400 is sold under the trade name Labview version 5.1 manufactured by National Instruments Corp. located in Austin, Tex. The equations for strain, load, stress, and loading energy follow. Note that much of the manipulated data is imported into a software program capable of graphing or further manipulating the data. A suitable software program for both graphing and manipulating the data is sold under the trade name Microsoft Excel 2000 manufactured by Microsoft Corporation located in Redmond, Wash.

Figure 11:
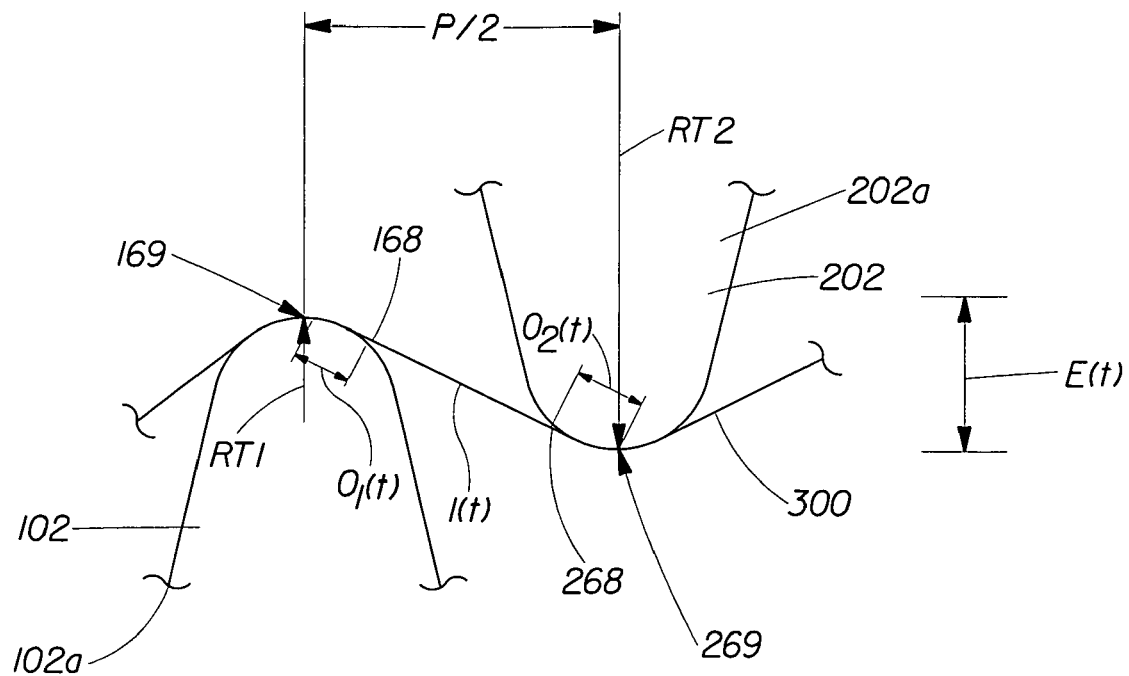
FIG. 11 is a schematic illustration of a first tooth and a second tooth on the first and second plates in engagement with a web material.
Figure 12:
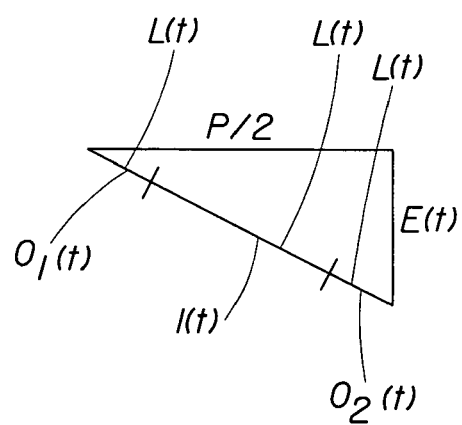
FIG. 12 is a schematic illustration of various dimensions illustrated in FIG. 11.

Strain (t) and strain rate (t) experienced by the workpiece during engagement by the first and second plates can be determined using equations which will be developed with reference to FIGS. 11 and 12. A first tooth 102 and a second tooth 202 on the first and second plates, respectively, are shown engaged with a workpiece 300 as shown in FIG. 11. A portion of the workpiece 300 extends between a center point 169 on the first tooth 102 to a center point 269 on the second tooth 202. The depth to which the teeth 102 and 202 are engaged is defined by E(t) as discussed previously. The initial gage length of the workpiece 300, prior to being stretched by the teeth 102 and 202, is equal to one-half of the pitch p of the teeth 102 and 202, i.e., p/2. The processed or stretched length of the workpiece 300 as a function of time, i.e., L(t), is determined using the following equation:

$$L(t)=O_1(t)+O_2(t)+I(t)$$

where $O_1(t)$ is equal to a section of the workpiece 300 engaged by the tooth 102 and extending from the tooth center point 169 to a final tooth tangent point 168;

where $O_2(t)$ is equal to a section of the workpiece 300 engaged by the tooth 202 and extending from the tooth center point 269 to a final tooth tangent point 268; and I(t) is equal to an intermediate section of the workpiece 300 not engaged by either tooth 102, 202 and extending between the final tooth tangent points 168 and 268. For all of the following equations, the variables as listed below are described as follows:

p is equal to the pitch of the teeth 102 and 202;

r is equal to the radius RT1 of the outer tip portion 102a of the tooth 102 and is also equal to the radius RT2 of the outer tip portion 202a of the tooth 202, see FIG. 11, as radii RT1 and RT2 are presumed to be equal; and E(t) is equal to the depth to which the teeth 102 and 202 have engaged one another as a function of time, and is determined by the equation which is further discussed in U.S. application Ser. No. 10/377,070, entitled "Ring Rolling Simulation Press" filed on Feb. 28, 2003.

I(t) is defined by the following equation:

$$I(t)=\sqrt{(p/2)^2+(E(t)-2r)^2}-(2r)^2$$

O(t) is defined by the following equations:

$$O(t)=O_1(t)+O_2(t).$$

When E(t)−2r>0, O(t) is defined by the following equation:

$$O(t)=\left[\pi-\alpha\ \cos\sqrt{\frac{(2r)^2}{(E(t)-2r)^2+(p/2)^2}}-\alpha\ \sin\sqrt{\frac{(p/2)^2}{(E(t)-2r)^2}}\right]\cdot 2r$$

When E(t)−2r≦0, O(t) is defined by the following equation:

$$O(t)=\left[-\alpha\ \cos\sqrt{\frac{(2r)^2}{(E(t)-2r)^2+(p/2)^2}}+\alpha\ \sin\sqrt{\frac{(p/2)^2}{(E(t)-2r)^2+(p/2)^2}}\right]\cdot 2r$$

When E(t)−2r>0, S(t) is defined by the following equations:

$$\text{Strain}(t)=\left(\frac{2\cdot O(t)+I(t)}{p/2}-1\right)$$

-continued $$\text{Strain}(t) = \left( \frac{\left( \pi - \alpha \cos\sqrt{\frac{(2r)^2}{(E(t)-2r)^2+(p/2)^2}} - \alpha \sin\sqrt{\frac{(p/2)^2}{(E(t)-2r)^2+(p/2)^2}} \right) \cdot}{(p/2)} \cdot \frac{2r + \sqrt{(p/2)^2+(E(t)-2r)^2-(2r)^2}}{(p/2)} - 1 \right)$$

When $E(t)-2r \leq 0$, $S(t)$ is defined by the following equations:

$$\text{Strain}(t) = \left( \frac{2 \cdot O(t) + I(t)}{p/2} - 1 \right)$$

$$\text{Strain}(t) = \left( \frac{\left( -\alpha \cos\sqrt{\frac{(2r)^2}{(E(t)-2r)^2+(p/2)^2}} + \alpha \sin\sqrt{\frac{(p/2)^2}{(E(t)-2r)^2+(p/2)^2}} \right) \cdot}{(p/2)} \cdot \frac{2r + \sqrt{(p/2)^2+(E(t)-2r)^2-(2r)^2}}{(p/2)} - 1 \right)$$

The average strain rate (t) can be determined by taking the first derivative of Strain(t). The first derivative of Strain(t) can be derived using, for example, a commercially available math processing software package such as Mathcad version 1.0 manufactured by Mathsoft Inc. located in Cambridge Mass.

Final strain ($S_f$) is defined by the following equation:

$$S_f = [(L_f - L_0)/L_0]$$

where $L_f$ is the final length, after processing, of the workpiece 300; and $L_0$ is the initial length, prior to processing, of the workpiece 300 that is equal to p/2.

$S_f$ is determined using the equation for Strain(t) with t=T.

It is believed that the first and second plates of the apparatus of the present invention can engage the workpiece 300 and stretch workpiece 300 at a strain rate up to about 2000/seconds.

Tensile force applied to the workpiece 300 by the teeth 102 and 202 can be determined from the following equations:

For $(E(t) - 2r) > 0$ $$F_{Mat} = \frac{(F_{LC})}{\cos\left[\alpha \sin\left[\frac{\left(\frac{p}{2}\right)^2}{\left(\frac{p}{2}\right)^2 + (E(t)-2\cdot r)^2}\right]^{0.5} + \alpha \cos\left[\frac{(2\cdot r)^2}{\left(\frac{p}{2}\right)^2+(E(t)-2\cdot r)^2}\right]^{0.5} - \frac{\pi}{2}\right]}$$

where:

$F_{LC}$ is equal to the combined force applied to the load cells 84; and the other variables have been discussed previously.

For $(E(t) - 2r) \leq 0$ $$F_{Mat} = \frac{(F_{LC})}{\cos\left[\frac{\pi}{2} - \alpha \sin\left[\frac{\left(\frac{p}{2}\right)^2}{\left(\frac{p}{2}\right)^2+(E(t)-2\cdot r)^2}\right]^{0.5} + \alpha \cos\left[\frac{(2\cdot r)^2}{\left(\frac{p}{2}\right)^2+(E(t)-2\cdot r)^2}\right]^{0.5}\right]}$$

where:

$F_{LC}$ is equal to the combined force applied to the load cells 84; and the other variables have been discussed previously.

The equation for $F_{Mat}$ provides the total force experienced by a workpiece. However, if the force per individual gage length is desired, then the $F_{Mat}$ should be divided by the number of gage lengths. An example of how to determine the number of gage lengths is multiplying the number of teeth for either the first or second set of teeth by two. Alternatively, another method may be to subtract two teeth from the total number of either the first or the second set of teeth and multiply by two. The two teeth subtracted may be considered as non-contributing based on slippage that may occur with two of the outer teeth.

Note that for the instance when $E(t)-2r=0$, either the equations for strain(t) and $F_{Mat}$ under the situations of $E(t)-2r \leq 0$ and $E(t)-2r \geq 0$ can be used to approximate strain(t) and $F_{Mat}$. Strain rate(t) becomes indeterminate when $E(t)-2r=0$ but can be solved by commercially available software programs or by hand. One suitable program, as mentioned above, is Mathcad.

The normal force experienced by the load cells, as discussed previously, is provided to the drive controller which provides the information to a processor/memory unit. Because the workpiece is being strained, work is being done on the workpiece during the engagement and disengagement segments of the simulation. Therefore, the normal force data in conjunction with the ram position data during engagement and disengagement collected by the processor/memory unit can be converted into work to express the amount of energy applied to and/or absorbed by the workpiece.

The activation energy for the workpiece is determined by integrating an area under a curve representing the normal force experienced by the load cell versus the ram position during the engagement and disengagement segments. The numerical integration by trapezoid rule can be used to estimate values under the curve mentioned previously. The equation is as follows:

$$E_a = \sum_{i=2}^{n}\left[(P_i - P_{i-1}) * \left(\frac{F_{n_i} + F_{n_{i-1}}}{2}\right)\right]$$

where:

n=the number of data points based on evenly spaced time slices;

P=Ram Position (m);

$F_n$=Load Cell Force (N); and $E_a$=total energy under the curve representing activation energy for the workpiece. Note that these variables apply to the equations listed below as well.

Another useful manipulation of the data provides a remaining amount of energy in a workpiece—the remaining amount of energy being termed residual energy. The residual energy is utilized for determining when a workpiece begins to breakdown and for determining the failure of the workpiece. For instance, when the carriage is at the "0 position", the workpiece has experienced no strain, therefore, the workpiece has 100% of its energy left. However, at 50% strain, the workpiece may only have 75% of its energy left. An example analysis of residual energy on a workpiece is provided below (see Example 6).

The residual energy of the workpiece is determined via the following equations. The activation energy up to the peak force is determined. Similar to the equation described above, the activation energy up to the peak force is determined via the trapezoid rule.

$$E_p = \sum_{i=2}^{n_p} \left[ (P_i - P_{i-1}) * \left( \frac{(F_{n_i} + F_{n_{i-1}})}{2} \right) \right]$$

where:

$n_p$=the number of data points up to the peak force experienced by the load cells.

$E_p$=the activation energy at the peak force experienced by the load cells.

The percent residual energy at any point beyond the peak can then be found by the following equation:

$$E_R = \left[ \frac{E_a - \sum_{i=2}^{n_r} \left[ (P_i - P_{i-1}) * \left( \frac{F_{n_i} + F_{n_{i-1}}}{2} \right) \right]}{E_a - E_p} \right] * 100$$

where:

$n_t$=number of points up to some time t, wherein t is the time of the evaluation of the percentage of residual energy.

$E_a$=activation energy described in the equation above;

$E_p$=the activation energy at the peak force experienced by the load cells; and $E_R$=the percent residual energy of the workpiece.

Note that the equations for residual energy above can also compare the activation energy up to a certain point to the entire area $E_a$ as opposed to the area remaining from $E_a$–$E_p$.

EXAMPLES

The measurements taken are carriage position by time and the load experienced by the load cells as described above. The strain experienced by the workpiece, the force exerted on the workpiece, the stress on the workpiece, the activation energy of the workpiece, and the residual energy of the workpiece, are all values which are derived from the data collected from the simulation apparatus.

Example 1

Figure 13:
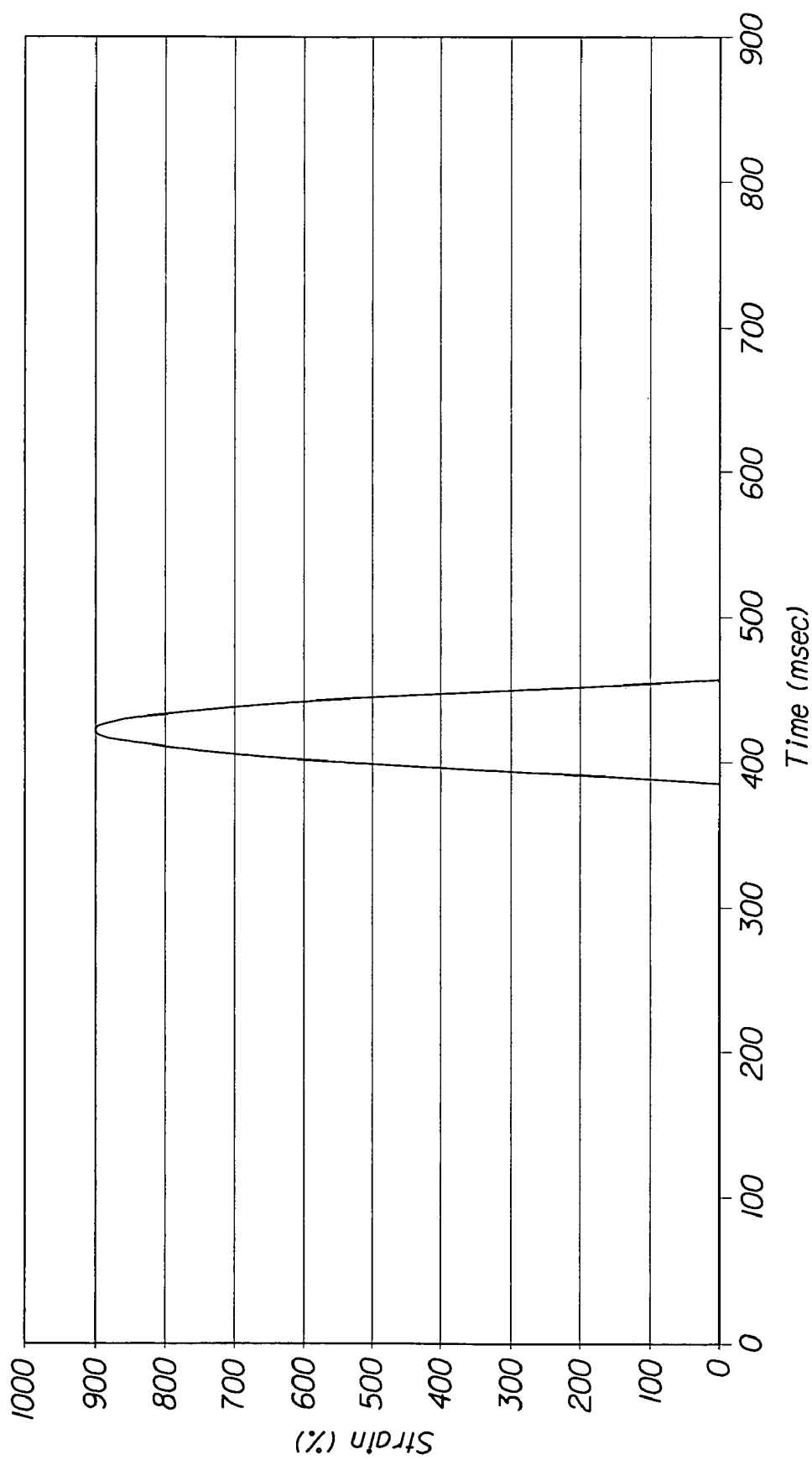
FIG. 13 is a plot of strain % versus time for Example 1.

A workpiece which included a film substrate was tested and taken to failure for examples 1–4. For example 1, the strain was calculated with respect to time. Note that the maximum strain occurred during the engagement segment of the simulation at approximately 400 milliseconds as shown in FIG. 13.

The variables input for this example were roll diameters of 152.4 mm, a web speed of 0.67 m/sec, a depth of engagement of 7.48 mm, a tooth pitch for both the first and second set of teeth was 1.524 mm, and a tip radius of 0.102 mm. The simulation was performed at a temperature of about 20° C.

Example 2

Figure 14:
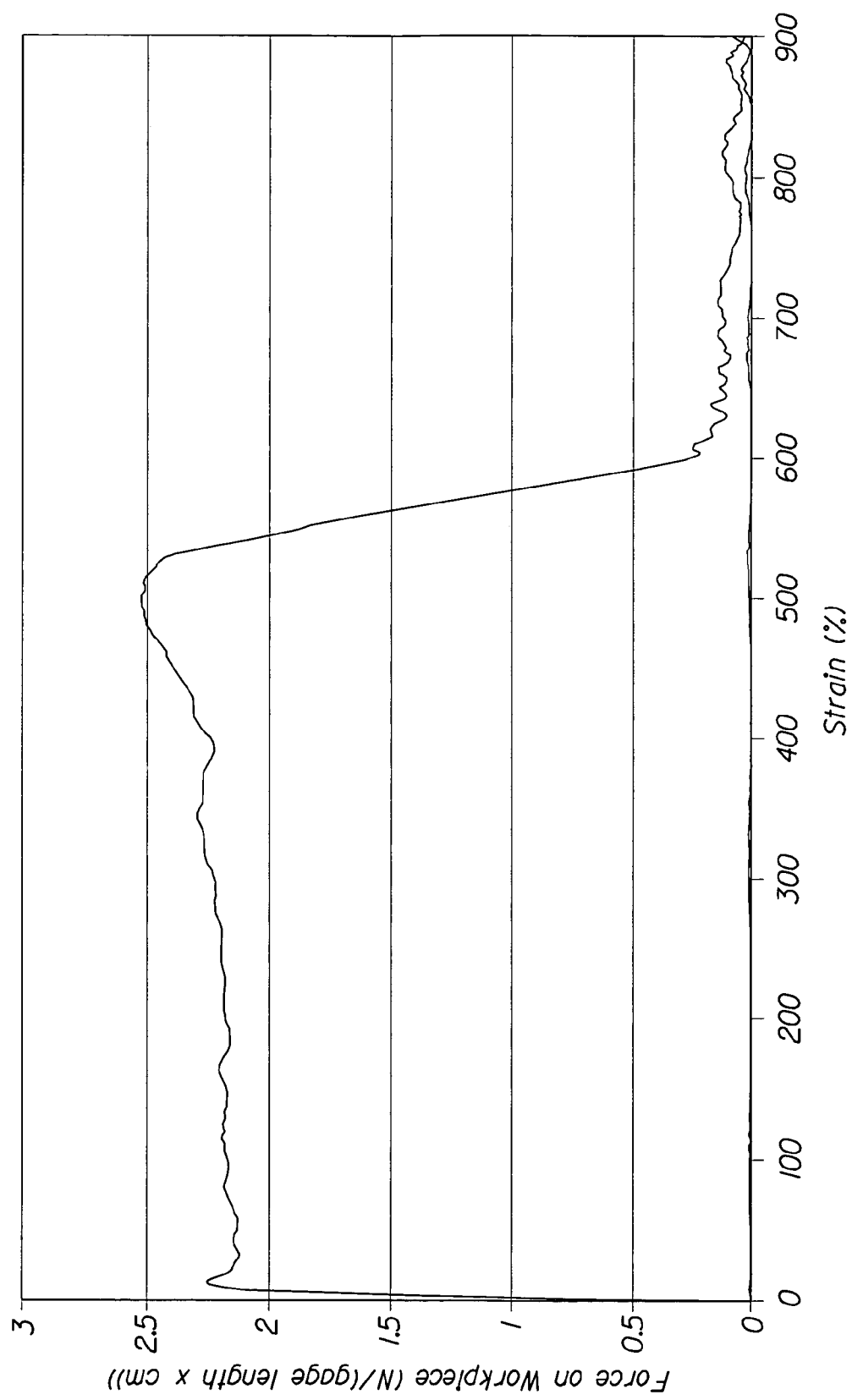
FIG. 14 is a plot of a force experienced by a workpiece versus a strain % on the workpiece for Example 2.

The force exerted on the workpiece of example 1 and the strain experienced by the workpiece of example 1 were derived from the simulation of the workpiece in example 1. The failure, i.e. where the film sample began to break, occurred at approximately 500% of strain as shown in FIG. 14.

Example 3

Figure 15:
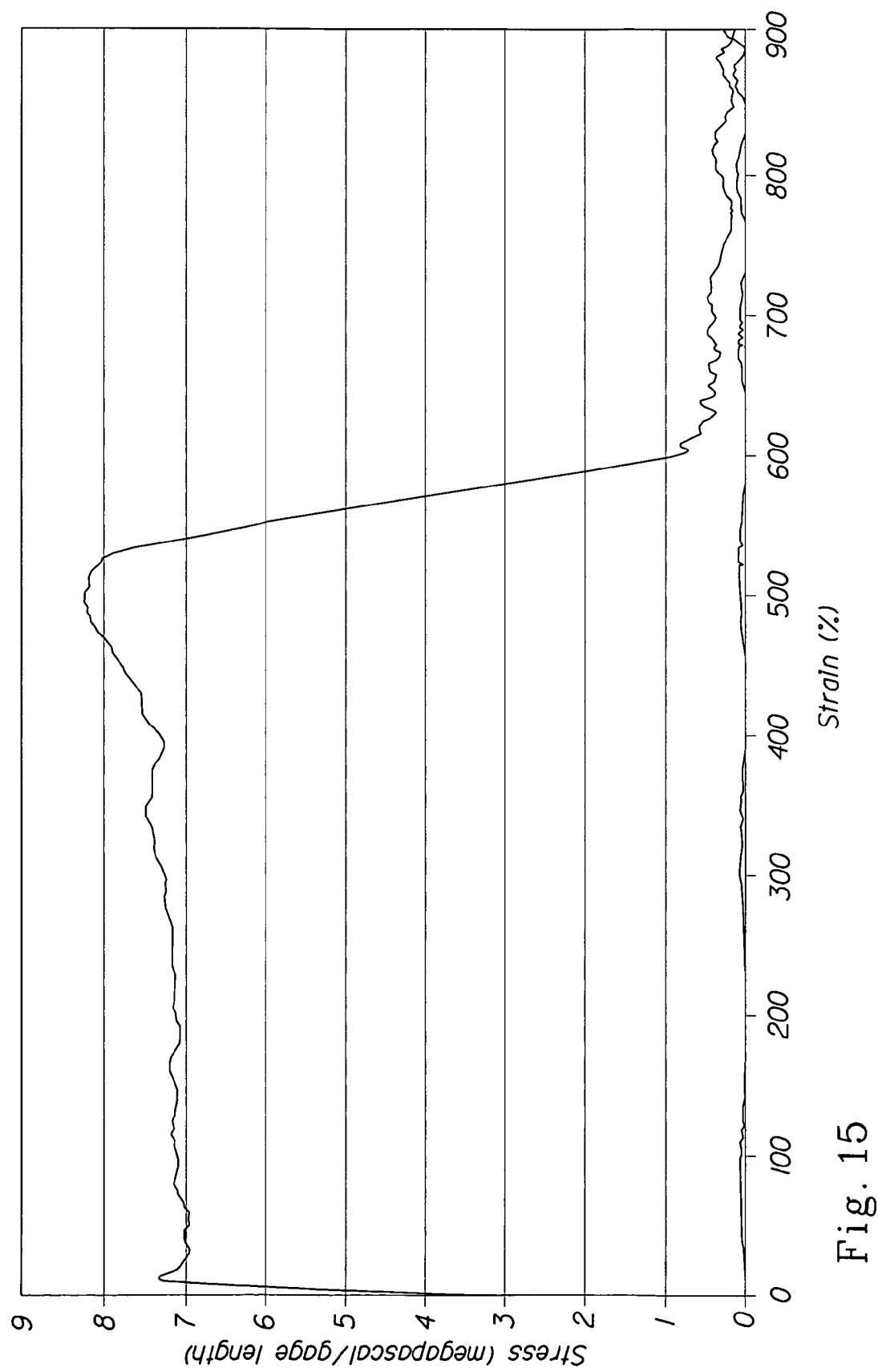
FIG. 15 is a plot of stress versus strain % for Example 3.

The stress experienced by the workpiece of example 1 is plotted against the percent strain experienced by the workpiece of example 1 is provided in this example. The stress is measured in mega pascals per gage length of the film substrate as shown in FIG. 15.

Example 4

Figure 16:
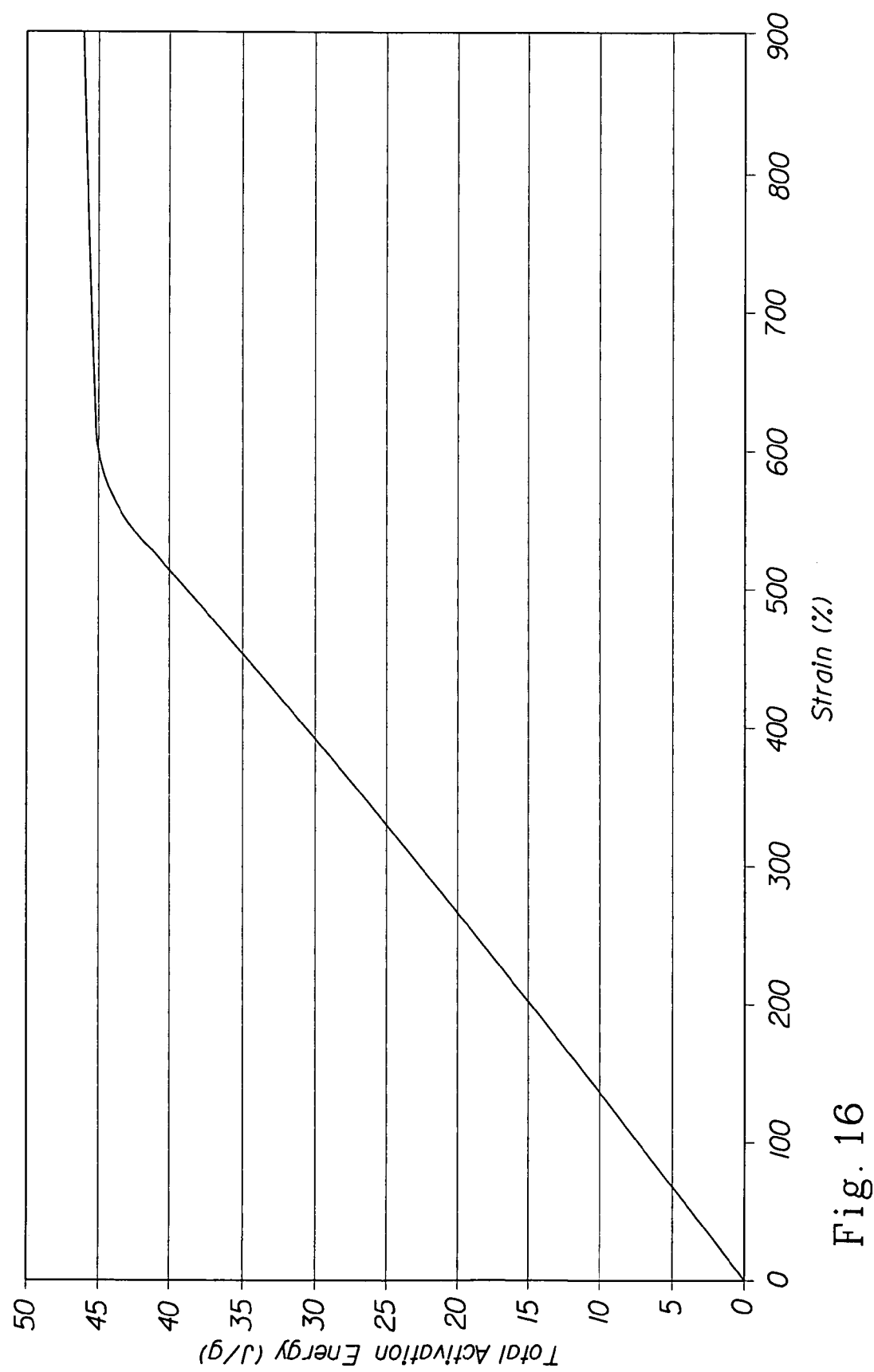
FIG. 16 is a plot of an activation energy of a workpiece verse a strain % on the workpiece for Example 4.

The activation energy of the workpiece of example 1 is plotted against the strain experienced by the workpiece of example 1 in this example. The plot only includes the activation energy regarding the engagement segment of the simulation and does not take into account the energy of the disengagement segment. The failure of the film, as mentioned previously for examples 2 and 3, occurs at approximately 500% strain; however, even beyond the failure of the film sample, there is still work performed on the film sample as shown in FIG. 16.

Example 5

Figure 17:
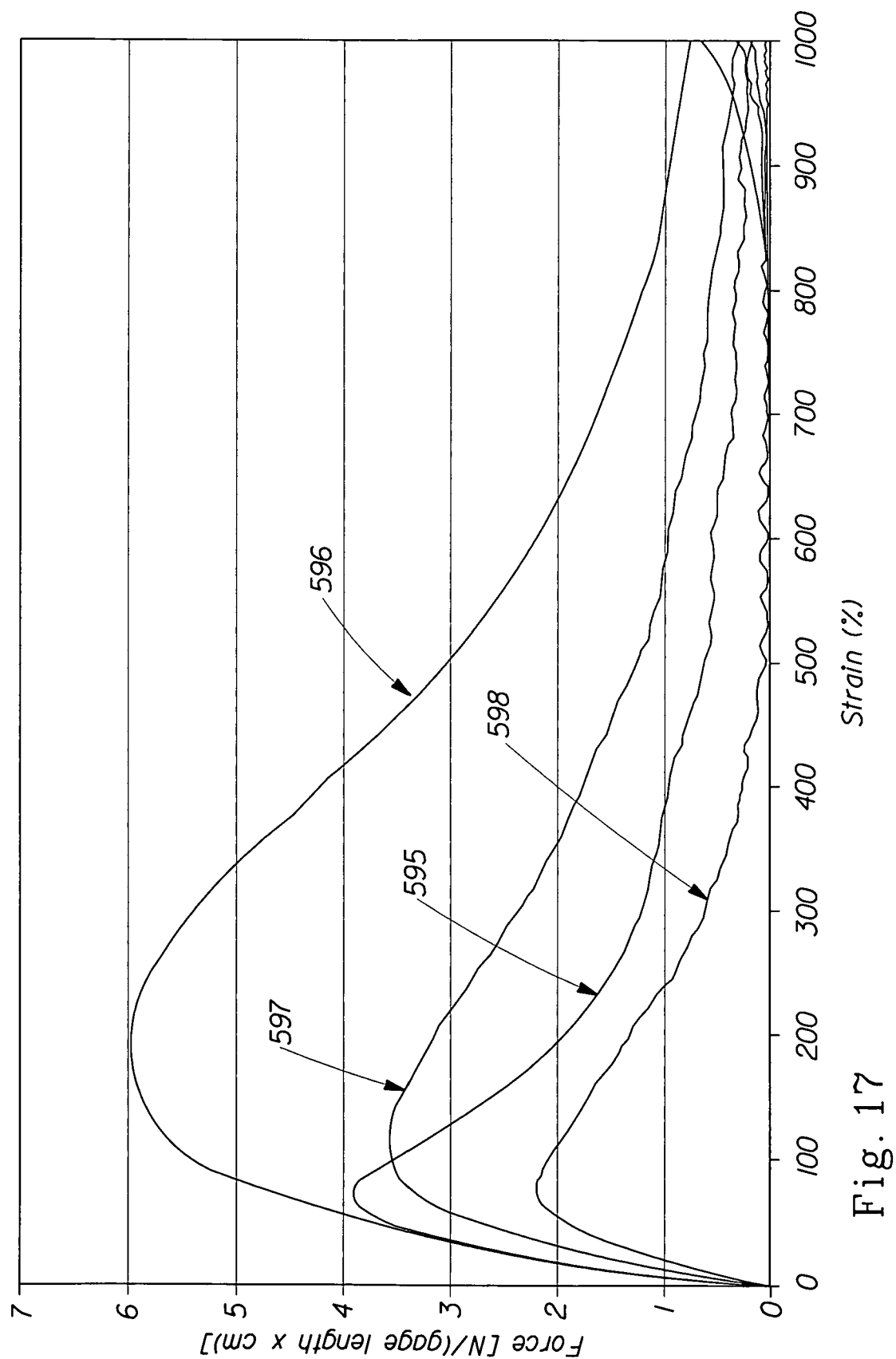
FIG. 17 is a plot of a force experienced by a workpiece versus a strain % experienced by a workpiece for multiple simulations while varying simulation parameters and conditions.

Workpieces comprising samples from a single nonwoven were utilized for this simulation. The simulation was performed four times showing the effect of various input (process) variables as well as simulation variables on the data. Specifically, the effect of the input variables and simulation variables on force experienced by the workpiece with respect to the strain experienced by the workpiece is shown in FIG. 17.

Curve 595 shows the force experienced by a first workpiece plotted against the strain experienced by the first workpiece. The input variables for this simulation were a teeth pitch for both the first and the second set of teeth of 1.524 mm and a maximum strain rate of 500 s$^{-1}$. The simulation was performed at about 20° C.

A second workpiece was used for the second simulation where the input variables were a teeth pitch for both the first and the second set of teeth of 1.524 mm and a maximum strain rate of 50 s$^{-1}$ (see curve 596). The simulation was also performed at about 20° C. Note the force experienced by the second workpiece increased by approximately 50% above that of the first workpiece subjected to a maximum strain rate of 500 s$^{-1}$.

A third workpiece was used for this simulation where the input variables were a teeth pitch for both the first and second set of teeth of 1.524 mm and a maximum strain rate of 500 s$^{-1}$ (see curve 597). However, the simulation was performed at a temperature of approximately 50° C.

A fourth workpiece was used for this simulation where the input variables were a teeth pitch for both the first and second set of teeth of 3.810 mm and a maximum strain rate of 500 s$^{-1}$ (see curve 598). The simulation was performed at a temperature of about 20° C. Note the marked reduction in the force experienced by the fourth workpiece by approximately 50% from the workpiece of curve 595.

Example 6

Figure 18:
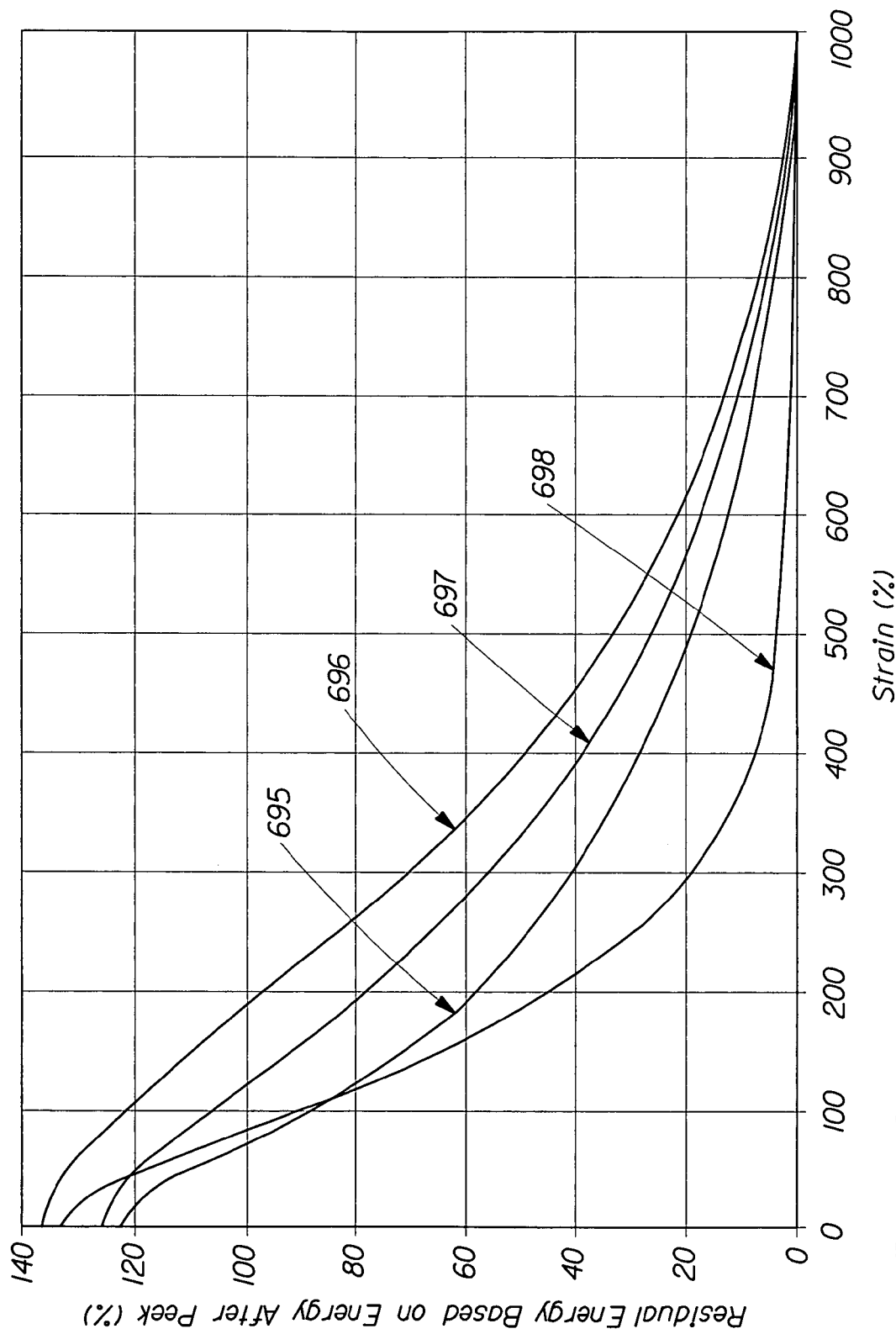
FIG. 18 is a plot of residual energy of a workpiece versus a strain % of the workpiece for multiple simulations while varying simulation parameters and conditions.

The simulations of example 5 were utilized to determine the residual energy of the various workpieces. The simulation was performed four times showing the effect of various input (process) variables as well as simulation variables on the data. Specifically, the effect of the input variables and simulation variables on the residual energy of the workpiece with respect to the percent strain experienced by the workpiece is shown in FIG. 18. Note the method employed utilizes the comparison of $E_R$ to $E_A - E_P$ as opposed to comparing $E_R$ to $E_A$.

Curve 695 shows the residual energy of the first workpiece, second workpiece, third workpiece, and fourth workpiece plotted against the percent strain experienced by each workpiece. Note that the first workpiece retains about 40% of it's residual energy at 300% strain. The second workpiece retains a residual energy of about 70% at a 300% strain as shown by curve 696. The third workpiece retains a residual energy of about 55% at 300% strain as shown by curve 697. The fourth workpiece retains a residual energy of about 20% at a 300% strain.

Example 7

A first workpiece comprising a laminate structure which included a first substrate and a second substrate was used in a first simulation. The first substrate and the second substrate were bonded together using an adhesive. A second simulation was performed using only the first and the second substrate in order to quantify the effect or interaction of the adhesive with the first and the second substrate. The input variables for the simulations were roll diameters of 152.4 mm, a web speed of 1.817 m/sec, a depth of engagement of 10.218 mm, and a teeth pitch for both the first and the second set of teeth of 3.810 mm. The simulations were run at approximately 20° C.

Figure 19:
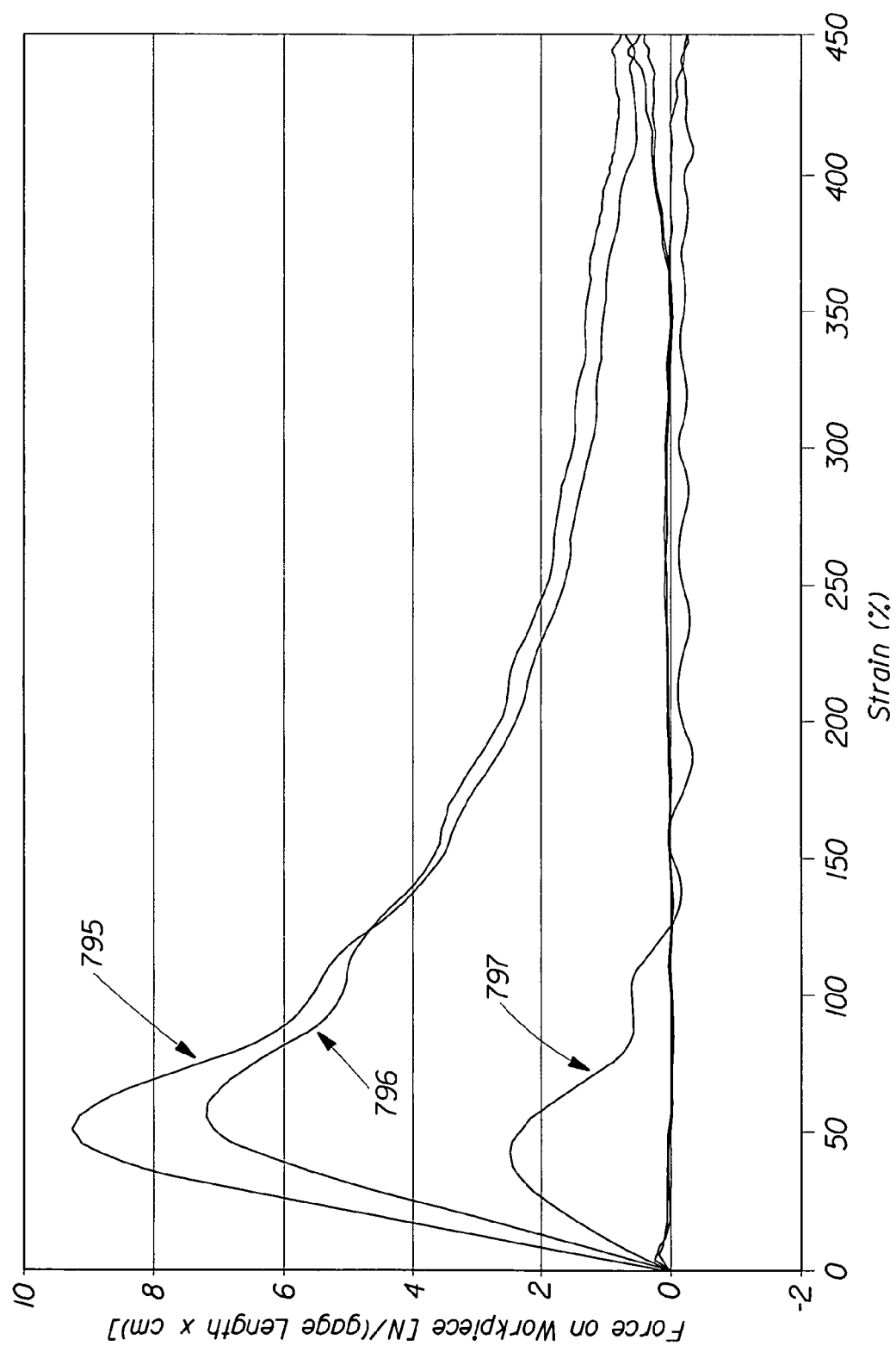
FIG. 19 is a plot comprising a simulation for a first and a second workpiece and the difference therebetween of the force experienced by the workpieces versus a strain % experienced by the workpieces.

The data acquired for the first simulation was stored and then processed such that the force experienced by the adhesively bonded laminate structure versus the strain experienced by the adhesively bonded laminate structure could be calculated (see FIG. 19, see curve 795). Similarly, the data acquired for the second simulation was stored and processed such that the force experienced by the first substrate and the second substrate versus the strain experienced by the first and second substrates could be calculated (curve 796).

The storage of the data further allows a software program or operator to then evaluate both the first and the second simulations and subtract the values of the adhesively bonded laminate from the values associated with the first and second substrate. This evaluation provides a curve 797 which represents the effect of the adhesive bonding on the first and second substrate.

Note that the values of the second simulation can be subtracted from the values of the first simulation either manually or via a software program. Suitable software programs for this subtraction have been described above, i.e. Labview version 5.1 or Microsoft Excel 2000 as discussed previously.

Example 8

Figure 20:
FIG. 20 is a plot of a force experienced by a workpiece versus a strain % of the workpiece for multiple simulations while varying a depth of engagement.

The prior examples simulated failure within each workpiece being tested. In this example, a workpiece is not subjected to failure but rather to loading and unloading at multiple depths of engagement as shown in FIG. 20. Three separate workpieces, which were samples from the same laminate structure, were subjected to distinct depths of engagement. So, the first workpiece was subjected to an engagement depth of 6 mm, the second workpiece was subjected to an engagement depth of 7 mm, and the third workpiece was subjected to an engagement depth of 8 mm.

The input variables were roll diameters of 152.4 mm, a web speed of 2.75 n/sec, and a teeth pitch for both the first and the second set of teeth of 3.810 mm. All of the simulations within this example were performed at approximately 20° C.

These simulations provide samples for analytical lab testing. Because these simulations mimic a ring rolling process that a workpiece would experience, these simulations reduce the likelihood that a particular workpiece may have to be implemented into the actual process to determine the compatibility of that workpiece with the ring rolling process. After the simulation, the workpiece can be inspected for physical defects which are related to product specifications or some external attribute which can be independently determined after the simulation. Specifically, after the simulation, the workpiece can be physically inspected for pinholes or other visual defects. The measure of these defects or other visual defects would in turn provide an objective measure by which a determination of the materials reaction to an actual ring rolling process could be made. Moreover, the sample may further be tested to determine the process' potential effect on the physical property of the workpiece, i.e. the cyclic hysteresis or percent set of the sample. Percent set is the growth in a material length or width after the simulation.

All documents cited in the Detailed Description of the Invention, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for inducing strain on a workpiece comprising the steps of:
providing a testing apparatus having a first set of teeth and a second set of teeth, wherein the first set of teeth are in communication with at least one load cell, wherein the second set of teeth are disposed on a movable carriage, and wherein a workpiece is disposed adjacent to the first or second set of teeth;

moving the movable carriage in accordance with a commanded position by time profile thereby linearly engaging the first set of teeth with the second set of teeth; and moving the movable carriage in accordance with the commanded position by time profile thereby linearly disengaging the first set of teeth with the second set of teeth.

2. The method of claim 1 further comprising the step of measuring an actual position of the carriage with respect to time.

3. The method of claim 2, wherein the commanded position of the movable carriage and the actual position of the movable carriage differ by no more than about +/−35 micrometers.

4. The method of claim 3, wherein the movable carriage linearly translates at a velocity which ranges from about +/−3000 mm/sec.

5. The method of claim 3, wherein the movable carriage can accelerate in a range of about +/−196 m/s$^2$.

6. The method of claim 3, wherein a load exerted by the movable carriage ranges from about +/−20,000 N.

7. The method of claim 1 further comprising the step of measuring a load experienced by the at least one load cell with respect to time.

8. The method of claim 7, further comprising the step of calculating a load experienced by the workpiece with respect to time.

9. The method of claim 7 further comprising the steps of calculating a strain by time, calculating a stress by time, and calculating a loading energy by time for the workpiece.

10. The method of claim 7, wherein the workpiece comprises a laminate structure having a first substrate bonded to a second substrate, the method further comprising the steps of:

providing a second workpiece disposed on the first or second set of teeth, wherein the second workpiece comprises a first substrate and a second substrate;

moving the movable carriage at a commanded position by time profile thereby linearly engaging the first set of teeth with the second set of teeth;

measuring a load experienced by the at least one load cell with respect to time;

moving the movable carriage at a commanded position by time profile thereby linearly disengaging the first set of teeth from the second set of teeth;

measuring a position of the movable carriage with respect to time;

calculating a load experienced by the second workpiece with respect to time; and subtracting the load experienced by the second workpiece with respect to time from the load experienced by the workpiece with respect to time.

11. The method of claim 1, wherein the workpiece comprises at least one of a nonwoven, a film, a paper, an adhesive, or combinations thereof.

12. The method of claim 10, wherein the second workpiece comprises at least one of a nonwoven, a film, a paper, an adhesive, or combinations thereof.

13. The method of claim 10 further comprising the steps of calculating a strain by time, calculating a stress by time, and calculating a loading energy by time for the second workpiece.

14. The method of claim 10, wherein the first substrate is bonded to the second substrate via an adhesive, wherein the method further comprises the step of calculating a load by strain, a stress by strain, a loading energy, or the loading energy by strain for the adhesive based on the difference of the load experienced by the second workpiece with respect to time and the load experienced by the workpiece with respect to time.

15. The method of claim 1 further comprising the step of utilizing the workpiece for analytical testing to determine physical properties such cyclic hysteresis, percent set, physical defects, and loading.

16. The method of claim 1, wherein the first set of teeth are disposed on a first heating plate and the second set of teeth are disposed on a second heating plate, and wherein the method further comprises the steps of moving the movable carriage such that the first set of teeth and the second set of teeth are proximate each other, heating the first heating plate and the second heating plate to about a desired temperature such that the workpiece is heated to about the desired temperature.

17. The method of claim 16, wherein the desired temperature ranges from about 20° C. to about 150° C.

18. The method of claim 1 wherein the testing apparatus induces a strain rate of greater than about 500 s$^{-1}$ on the workpiece.

* * * * *

UNITED STATES PATENT AND TRADEMARK OFFICE
CERTIFICATE OF CORRECTION

PATENT NO. : 7,024,939 B2
APPLICATION NO. : 10/942487
DATED : April 11, 2006
INVENTOR(S) : Barry Jay Anderson et al.

It is certified that error appears in the above-identified patent and that said Letters Patent is hereby corrected as shown below:

Column 1

Line 14, delete ",843,134" and insert -- 6,843,134 --.

Column 3

Line 46, delete "verse" and insert -- versus --.

Column 12

Beginning at line 40, delete formula

"$$O(t) = \left[ \pi - a\cos\sqrt{\frac{(2r)^2}{(E(t)-2r)^2 + (p/2)^2}} - a\sin\sqrt{\frac{(p/2)^2}{(E(t)-2r)^2}} \right] \cdot 2r$$"

and insert formula $$--O(t) = \left[ \pi - a\cos\sqrt{\frac{(2r)^2}{(E(t)-2r)^2 + (p/2)^2}} - a\sin\sqrt{\frac{(p/2)^2}{(E(t)-2r)^2 + (p/2)^2}} \right] \cdot 2r --.$$

Column 13

Line 34, delete "1.0" and insert -- 11.0 --.

Column 18

Line 24, delete "n/sec" and insert -- m/sec --.

Signed and Sealed this

Seventh Day of August, 2007

JON W. DUDAS
*Director of the United States Patent and Trademark Office*